United States Patent [19]

Coates et al.

[11] Patent Number: 5,183,820

[45] Date of Patent: Feb. 2, 1993

[54] LACTAM DERIVATIVES

[75] Inventors: Ian H. Coates, Hertford; Alexander W. Oxford; Peter C. North, both of Royston; Barry J. Price, Tewin Wood, all of England

[73] Assignee: Glaxo Group Limited, London, England

[21] Appl. No.: 691,814

[22] Filed: Apr. 26, 1991

Related U.S. Application Data

[63] Continuation of Ser. No. 387,180, Aug. 1, 1989, abandoned.

[30] Foreign Application Priority Data

Aug. 2, 1988 [GB] United Kingdom ............... 8818393
Feb. 23, 1989 [GB] United Kingdom ............... 8904195
Feb. 28, 1989 [GB] United Kingdom ............... 8904550

[51] Int. Cl.$^5$ .................. A61K 31/55; C07D 401/14
[52] U.S. Cl. .................................. 514/292; 514/215; 540/521; 546/86
[58] Field of Search ............... 514/215, 292; 546/86; 540/521

[56] References Cited

U.S. PATENT DOCUMENTS

| | | | |
|---|---|---|---|
| 4,636,563 | 1/1987 | Abou-Gharbia | 546/87 |
| 4,695,578 | 9/1987 | Coates et al. | 514/397 |
| 4,725,615 | 2/1988 | Coates et al. | 514/397 |
| 4,749,718 | 6/1988 | Coates et al. | 514/397 |
| 4,754,038 | 6/1988 | Abou-Gharbia | 546/87 |
| 4,798,896 | 1/1989 | Abou-Gharbia et al. | 546/87 |
| 4,808,581 | 2/1989 | Oxford et al. | 514/212 |
| 4,814,344 | 3/1989 | Humber et al. | 514/397 |
| 4,822,881 | 4/1989 | Coates et al. | 540/603 |
| 4,859,662 | 8/1989 | Coates et al. | 514/212 |
| 4,918,080 | 4/1990 | Oxford et al. | 514/300 |
| 4,939,144 | 7/1990 | Coates et al. | 514/212 |

FOREIGN PATENT DOCUMENTS

238411-A1 9/1987 European Pat. Off.
306323 3/1989 European Pat. Off.
3920857 9/1964 Japan.
2180535B 4/1987 United Kingdom.

OTHER PUBLICATIONS

Abou-Gharbia et al., *J. Med. Chem.*, 1987, 30, 1818–1823.

*Primary Examiner*—Mary C. Lee
*Assistant Examiner*—Jacqueline Haley
*Attorney, Agent, or Firm*—Bacon & Thomas

[57] ABSTRACT

The invention provides potent and selective antagonists of 5-HT at 5-HT$_3$ receptors which are tricyclic lactams of the formula (I)

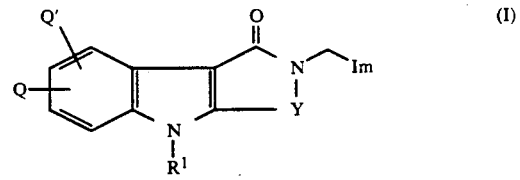

wherein Im represents an imidazolyl group of the formula:

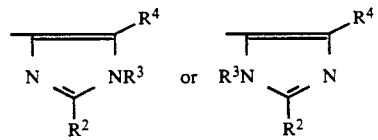

and R$^1$ represents a hydrogen atom or a group selected from C$_{1-6}$alkyl, C$_{3-6}$alkenyl, C$_{3-10}$alkynyl, C$_{3-7}$cycloalkyl, C$_{3-7}$cycloalkylC$_{1-4}$alkyl, phenyl, phenylC$_{1-3}$alkyl, —CO$_2$R$^5$, —COR$^5$, —CONR$^5$R$^6$ or —SO$_2$R$^5$;

one of the groups represented by R$^2$, R$^3$ and R$^4$ is a hydrogen atom or a C$_{1-6}$alkyl, C$_{3-7}$cycloalkyl, C$_{3-6}$alkenyl, phenyl or phenylC$_{1-3}$alkyl group, and each of the other two groups, which may be same or different, represents a hydrogen atom or a C$_{1-6}$alkyl group;

Y represents the group CH=CH or (CH$_2$)$_n$, wherein n represents 2 or 3;

Q represents a halogen atom, or a group selected from hydroxy, C$_{1-4}$alkoxy, phenylC$_{1-3}$alkoxy, C$_{1-6}$alkyl, cyano, phenyl which may be unsubstituted or substituted by one or more C$_{1-4}$alkyl, C$_{1-4}$alkoxy or hydroxy groups or halogen atoms, —NR$^7$R$^8$, —CONR$^7$R$^8$, —(CH$_2$)$_p$CONR$^7$R$^8$, —(CH$_2$)$_q$NR$^9$R$^{10}$ or —(CH$_2$)$_2$CO$_2$R$^{11}$;

Q' represents a hydrogen or a fluorine atom;

and physiologically acceptable salts and solvates thereof.

20 Claims, No Drawings

LACTAM DERIVATIVES

This application is a continuation of application Ser. No. 07/387,180, filed Aug. 1, 1989, now abandoned.

This invention relates to lactam derivatives, to processes for their preparation, to pharmaceutical compositions containing them and to their medical use.

In particular the invention relates to compounds which are potent and selective antagonists of 5-hydroxytryptamine (5-HT) at 5-HT receptors of the type located on terminals of primary afferent nerves. Receptors of this type are now designated as $5\text{-}HT_3$ receptors and are also present in the central nervous system. 5-HT occurs widely in the neuronal pathways in the central nervous system and disturbance of these 5-HT containing pathways is known to alter behavioural syndromes such as mood, psychomotor activity, appetite and memory.

Compounds having antagonist activity at $5\text{-}HT_3$ receptors have been described previously.

Thus for example German Offenlegungsschrift No. 3740352 discloses compounds which may be represented by the general formula:

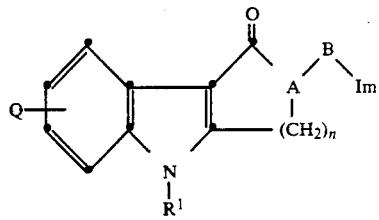

wherein Im represents an imidazolyl group of the formula:

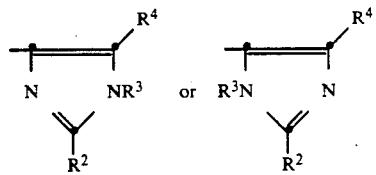

$R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl-, phenyl, phenyl$C_{1-3}$alkyl-, $-CO_2R^5$, $-COR^5$, $-CONR^5R^6$ or $-SO_2R^5$ (wherein $R^5$ and $R^6$, which may be the same or different, each represents a hydrogen atom, a $C_{1-6}$alkyl or $C_{3-7}$cycloalkyl group, or a phenyl or phenyl$C_{1-4}$alkyl- group, in which the phenyl group is optionally substituted by one or more $C_{1-4}$alkyl, $C_{1-4}$alkoxy or hydroxy groups or halogen atoms, with the proviso that $R^5$ does not represent a hydrogen atom when $R^1$ represents a group $-CO_2R^5$ or $-SO_2R^5$);

one of the groups represented by $R^2$, $R^3$ and $R^4$ is a hydrogen atom or a $C_{1-6}$alkyl, $C_{3-7}$cycloalkyl, $C_{3-6}$alkenyl, phenyl or phenyl$C_{1-3}$alkyl- group, and each of the other two groups, which may be the same or different, represents a hydrogen atom or a $C_{1-6}$alkyl group; Q represents a hydrogen or a halogen atom, or a hydroxy, $C_{1-4}$alkoxy, phenyl$C_{1-3}$alkoxy- or $C_{1-6}$alkyl group or a group $-NR^7R^8$ or $-CONR^7R^8$ (wherein $R^7$ and $R^8$, which may be the same or different, each represents a hydrogen atom or a $C_{1-4}$alkyl or $C_{3-4}$alkenyl group, or together with the nitrogen atom to which they are attached form a saturated 5 to 7 membered ring);

n represents 1, 2 or 3;

and A-B represents the group $CH-CH_2$ or $C=CH$; and physiologically acceptable salts and solvates thereof.

We have now found a novel group of compounds which differ in structure from those described previously, and which are potent antagonists of the effect of 5-HT at $5\text{-}HT_3$ receptors.

The present invention provides a tricyclic lactam of the general formula (I):

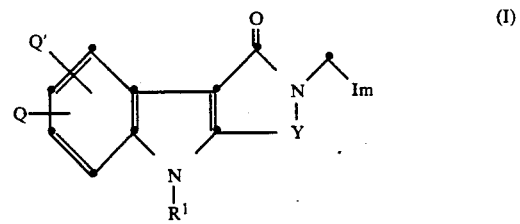

wherein Im represents an imidazolyl group of the formula:

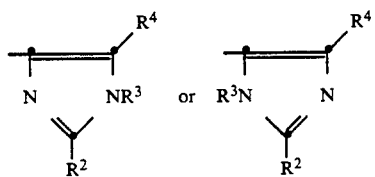

and $R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl-, phenyl, phenyl$C_{1-3}$alkyl-, $-CO_2R^5$, $-COR^5$, $-CONR^5R^6$ or $-SO_2R^5$ (wherein $R^5$ and $R^6$, which may be the same or different, each represents a hydrogen atom, a $C_{1-6}$alkyl or $C_{3-7}$cycloalkyl group, or a phenyl or phenyl$C_{1-4}$alkyl- group, in which the phenyl group is optionally substituted by one or more $C_{1-4}$alkyl, $C_{1-4}$alkoxy or hydroxy groups or halogen atoms, with the proviso that $R^5$ does not represent a hydrogen atom when $R^1$ represents a group $-CO_2R^5$ or $-SO_2R^5$);

one of the groups represented by $R^2$, $R^3$ and $R^4$ is a hydrogen atom or a $C_{1-6}$alkyl, $C_{3-7}$cycloalkyl, $C_{3-6}$alkenyl, phenyl or phenyl$C_{1-3}$alkyl- group, and each of the other two groups, which may be the same or different, represents a hydrogen atom or a $C_{1-6}$alkyl group;

Y represents the group $CH=CH$ or $(CH_2)_n$, wherein n represents 2 or 3;

Q represents a halogen atom, or a group selected from hydroxy, $C_{1-4}$alkoxy, phenyl$C_{1-3}$alkoxy-, $C_{1-6}$alkyl, cyano, phenyl which may be unsubstituted or substituted by one or more $C_{1-4}$alkyl, $C_{1-4}$alkoxy or hydroxy groups or halogen atoms, $-NR^7R^8$, $-CONR^7R^8$ or $-(CH_2)_pCONR^7R^8$ (wherein $R^7$ and $R^8$, which may be the same or different, each represents a hydrogen atom or a $C_{1-4}$alkyl or $C_{3-4}$alkenyl group, or together with the nitrogen atom to which they are attached form a saturated 5 to 7 membered ring; and p represents 1, 2 or 3), $-(CH_2)_qNR^9R^{10}$ (wherein $R^9$ represents a hydrogen atom or a $C_{1-4}$alkyl group, and R[10] represents a group —COR[11] or —SO₂R[11] wherein R[11] represents a C₁₋₄alkyl group; and q represents 0, 1, 2 or 3), or —(CH₂)₂CO₂R[11] (R[11] being as defined previously);

Q' represents a hydrogen or a fluorine atom; and physiologically acceptable salts and solvates thereof.

According to one aspect, the invention provides compounds of formula (I) wherein Y represents the group (CH₂)ₙ, Q' represents a hydrogen atom, and Q represents a halogen atom or a group selected from hydroxy, C₁₋₄alkoxy, phenylC₁₋₃alkoxy-, C₁₋₆alkyl, —NR⁷R⁸ or —CONR⁷R⁸ (R⁷, R⁸, R¹ and IM being as defined in formula (I)).

According to another aspect, the invention provides compounds of formula (I) wherein Y represents the group CH═CH, Q' represents a hydrogen atom, and Q represents a halogen atom or a group selected from hydroxy, C₁₋₄alkoxy, phenylC₁₋₃alkoxy-, C₁₋₆alkyl, —NR⁷R⁸ or —CONR⁷R⁸ (R⁷, R⁸, R¹ and Im being as defined in formula (II)).

According to yet another aspect, the invention provides compounds of formula (I) wherein Q' represents a hydrogen atom and Q represents a group selected from cyano, phenyl which may be unsubstituted or substituted by one or more C₁₋₄alkyl, C₁₋₄alkoxy or hydroxy groups or halogen atoms, —(CH₂)ₚCONR⁷R⁸ or —(CH₂)qNR⁹R¹⁰(p,q, R⁷, R⁸, R⁹, R¹⁰, R¹, Im and y being as defined in formula (I)).

Suitable physiologically acceptable salts of the compounds of general formula (I) include acid addition salts formed with organic or inorganic acids for example, hydrochlorides, hydrobromides, sulphates, alkyl- or arylsulphonates (e.g. methanesulphonates or p-toluenesulphonates), phosphates, acetates, citrates, succinates, tartrates, fumarates and maleates. The solvates may, for example, be hydrates.

All optical isomers of compounds of general formula (I) and their mixtures including the racemic mixtures thereof, and all the geometric isomers of compounds of formula (I), are embraced by the invention.

Referring to the general formula (I), an alkyl group may be a straight chain or branched chain alkyl group, for example, methyl, ethyl, n-propyl, prop-2-yl, n-butyl, but-2-yl, 2-methylprop-2-yl, n-pentyl, pent-3-yl or n-hexyl. A C₃₋₆alkenyl group may be, for example, a propenyl or butenyl group. When R¹ represents a C₃₋₆alkenyl or C₃₋₁₀alkynyl group, or R³ represents a C₃₋₆alkenyl group, or R⁷ or R⁸ represents a C₃₋₄alkenyl group, the double or triple bond may not be adjacent to the nitrogen atom. A phenylC₁₋₃alkyl- group may be, for example, a benzyl, phenethyl or 3-phenylpropyl group. A C₃₋₇cycloalkyl group may be, for example, a cyclopropyl, cyclobutyl, cyclopentyl, cyclohexyl or cycloheptyl group. A C₁₋₄alkoxy group may be, for example, a methoxy group. A halogen atom may be, for example, a fluorine, chlorine or bromine atom.

The substituents Q and Q' may be at the a, b, c or d-position of the indole moiety. Q is preferably at the d-position, and when Q' is a fluorine atom, Q' is preferably at the a-position.

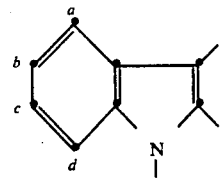

A preferred class of compounds of formula (I) is that wherein R¹ represents a hydrogen atom or a C₁₋₆alkyl (e.g. methyl or isopropyl), C₃₋₄alkynyl (e.g. prop-2-ynyl), C₄₋₆cycloalkylmethyl (e.g. cyclopentylmethyl) or C₁₋₃alkylsulphonyl (e.g. methylsulphonyl) group. More preferably R¹ represents a hydrogen atom or a C₁₋₄alkyl (e.g. methyl or isopropyl), C₃₋₄alkynyl (e.g. prop-2-ynyl) or C₄₋₆cycloalkylmethyl (e.g. cyclopentylmethyl)group.

Another preferred class of compounds of formula (I) is that wherein R² represents a hydrogen atom or a C₁₋₄alkyl (e.g. methyl) group, more preferably a hydrogen atom.

Another preferred class of compounds of formula (I) is that wherein R³ represents a hydrogen atom or a C₁₋₄alkyl (e.g. methyl) group, more preferably a hydrogen atom.

A further preferred class of compounds of formula (I) is that wherein R⁴ represents a hydrogen atom or a C₁₋₄alkyl (e.g. methyl or n-propyl) group. More preferably R⁴ represents a C₁₋₄alkyl (e.g. methyl or n-propyl) group. Most preferably R⁴ represents a methyl group.

Another preferred class of compounds of formula (I) is that in which Q represents a halogen (e.g. fluorine or bromine) atom, or a hydroxy, C₁₋₄alkoxy (e.g. methoxy), phenylC₁₋₃alkoxy- (e.g. phenylmethoxy), C₁₋₆alkyl (e.g. methyl), cyano, phenyl, —CONH₂ or —(CH₂)₂CO₂CH₃ group. More preferably Q represents a halogen (e.g. fluorine or bromine) atom, or a hydroxy, phenylC₁₋₃alkoxy- (e.g. phenylmethoxy), C₁₋₃alkyl (e.g. methyl) or cyano group. Most preferably Q represents a fluorine atom.

A further preferred class of compound of formula (I) is that in which Q' represents a hydrogen atom. When Q' represents a fluorine atom, Q preferably represents a halogen (e.g. fluorine) atom.

Yet another preferred class of compounds of formula (I) is that in which Y represents the group (CH₂)₂.

A preferred group of compounds of formula (I) is that wherein R¹ represents a hydrogen atom or a C₁₋₆alkyl, C₃₋₄alkynyl, C₄₋₆cycloalkylmethyl or C₁₋₃alkylsulphonyl group; R² represents a hydrogen atom; R³ represents a hydrogen atom or a C₁₋₄alkyl group; R⁴ represents a C₁₋₄alkyl group; and Q represents a halogen atom or a hydroxy, C₁₋₄alkoxy, phenylC₁₋₃alkoxy-, C₁₋₆alkyl, cyano, phenyl, —CONH₂ or —(CH₂)₂CO₂CH₃ group.

A particularly preferred group of compounds of formula (I) is that wherein R¹ represents a hydrogen atom or a C₁₋₄alkyl (e.g. methyl or isopropyl), C₃₋₄alkynyl (e.g. prop-2-ynyl) or C₄₋₆cycloalkylmethyl (e.g. cyclopentylmethyl) group; R² and R³ each represent a hydrogen atom; R⁴ represents a C₁₋₄alkyl (e.g. methyl or n-propyl) group; and Q represents a halogen (e.g. fluorine or bromine) atom or a hydroxy, phenylC₁₋₃alkoxy- (e.g. phenylmethoxy), C₁₋₃alkyl (e.g. methyl) or cyano group.

Within the above preferred and particularly preferred groups of compounds, an especially important group of compounds is that in which Y represents the group (CH$_2$)$_2$ and Q' is a hydrogen atom.

Preferred compounds according to the invention are:
6-fluoro-2,3,4,5-tetrahydro-5-methyl-2-[(5-methyl-1H-imidazol-4-yl)methyl]-1H-pyrido[4,3-b]indol-1-one;
2,3,4,5-tetrahydro-5,6-dimethyl-2-[(5-methyl-1H-imidazol-4-yl)methyl]-1H-pyrido[4,3-b]indol-1-one;
6,9-difluoro-2,3,4,5-tetrahydro-5-methyl-2-[(5-methyl-1H-imidazol-4-yl)methyl]-1H-pyrido[4,3-b]indol-1-one;
6-fluoro-2,3,4,5-tetrahydro-2-[(5-methyl-1H-imidazol-4-yl)methyl]-5-(2-propynyl)-1H-pyrido[4,3-b]indol-1-one;
2,3,4,5-tetrahydro-5-methyl-2-[(5-methyl-1H-imidazol-4-yl)methyl]-1-oxo-1H-pyrido[4,3-b]indole-6-carbonitrile;
and their physiologically acceptable salts and solvates.

The potent and selective antagonism of 5-HT at 5-HT$_3$ receptors by compounds of the invention has been demonstrated by their ability to inhibit 3-(5-methyl-1H-imidazol-4-yl)-1-[1-(methyl-t$_3$)-1H-indol-3-yl]-1-propanone binding in rat entorhinal cortex homogenates (following the general procedure described by G. Kilpatrick et al. in *Nature*, 1987, 330, 746), and/or by their ability to inhibit the 5-HT-induced depolarisation of the rat isolated vagus nerve preparation.

In addition to their activity as potent and selective antagonists of 5-HT at 5-HT$_3$ receptors, certain compounds according to the invention have the advantage of an extended duration of action.

A particularly preferred compound on account of both its potency and duration of action is 6-fluoro-2,3,4,5-tetrahydro-5-methyl-2-[(5-methyl-1H-imidazol-4-yl)methyl]-1H-pyrido[4,3-b]indol-1-one and its physiologically acceptable salts and solvates. Preferred salts of this compound are the hydrochloride, maleate and benzoate.

Compounds of formula (I), which antagonise the effect of 5-HT at 5-HT$_3$ receptors, are useful in the treatment of conditions such as psychotic disorders (e.g. schizophrenia and mania); anxiety; and nausea and vomiting, particularly that associated with cancer chemotherapy and radiotherapy. Compounds of formula (I) are also useful in the treatment of gastric stasis; symptoms of gastrointestinal dysfunction such as occur with dyspepsia, peptic ulcer, reflux oesophagitis, flatulence and irritable bowel syndrome; migraine; obesity and conditions such as bulimia; and pain. Compounds of formula (I) may also be used in the treatment of dependency on drugs and substances of abuse, depression, and dementia and other cognitive disorders.

According to another aspect, the invention provides a method of treatment of a human or animal subject suffering from a psychotic disorder such as schizophrenia or mania; or from anxiety; nausea or vomiting; gastric stasis; symptoms of gastrointestinal dysfunction such as dyspepsia, reflux oesophagitis, peptic ulcer, flatulence and irritable bowel syndrome; migraine; obesity and conditions such as bulimia; pain; dependency on drugs or substances of abuse; depression; or dementia or another cognitive disorder which comprises administering an effective amount of a compound of formula (I) or a physiologically acceptable salt or solvate thereof.

Accordingly, the invention also provides a pharmaceutical composition which comprises at least one compound selected from compounds of the general formula (I), and their physiologically acceptable salts and solvates (e.g. hydrates), for use in human or veterinary medicine, and formulated for administration by any convenient route.

Such compositions may be formulated in conventional manner using one or more physiologically acceptable carriers and/or excipients.

Thus the compounds according to the invention may be formulated for oral, buccal, parenteral or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxylpropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by bolus injection or continuous infusion. Formulations for injection may be presented in unit dosage from e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

In addition to the formulations described previously, the compounds of the invention may also be formulated as depot preparations. Such long acting formulations may be administered by implementation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For administration by inhalation the compounds according to the invention are conveniently delivered in the form of an aerosol spray presentation from pressurised packs or a nebuliser, with the use of a suitable propellant, e.g. dichlorodifluoromethane, trichloroflouromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

For intranasal administration, the compounds according to the invention may be formulated as solutions for administration via a suitable method or unit dose device or alternatively as a powder mix with a suitable carrier for administration using a suitable delivery device.

The compounds of formula (I) may also be administered in combination with other therapeutic agents. Thus, for example, in the treatment of gastric stasis, symptoms of gastrointestinal dysfunction and nausea and vomiting, the compounds of formula (I) may be administered in combination with antisecretory agents such as histamine $H_2$-receptor antagonists (e.g. ranitidine, sufotidine, cimetidine, famotidine, nizatidine or roxatidine) or $H+K+ATPase$ inhibitors (e.g. omeprazole). In the treatment of nausea and vomiting, compounds of formula (I) may also be administered in combination with dexamethasone or a cyclo-oxygenase inhibitor such as piroxicam.

A proposed dose of the compounds of the invention for administration to man (of approximately 70 kg body weight) is 0.001 to 100 mg, preferably 0.01 to 50 mg, more preferably 0.1 to 20 mg of the active ingredient per unit dose expressed as the weight of free base, which could be administered, for example, 1 to 4 times per day. It will be appreciated that it may be necessary to make routine variations to the dosage, depending on the age and condition of the patient. The dosage will also depend on the route of administration.

Compounds of general formula (I) and physiologically acceptable salts or solvates thereof may be prepared by the general methods outlined hereinafter. In the following description, the groups $R^1$, Y, Q,Q' and Im are as defined for compounds of general formula (I) unless otherwise stated.

According to a first general process (A), a compound of general formula (I) may be prepared by alkylating a compound of formula (II):

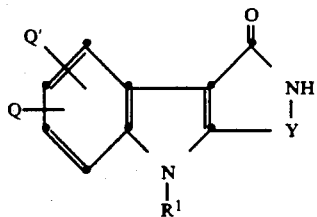

(II)

with a compound of formula (III):

X—Im    (III)

or a protected derivative thereof, wherein X represents a group —$CH_2L$ and L represents a leaving atom or group, such as a halogen atom (e.g. chlorine, bromine or iodine), or an acyloxy group (e.g. trifluoroacetyloxy or acetoxy), or a sulphonyloxy group (e.g. trifluoromethanesulphonyloxy, p-toluenesulphonyloxy or methanesulphonyloxy) and the reaction is effected in the presence of a base; or X represents the group —$CH_2OH$ and the reaction is effected in the presence of an acid at an elevated temperature, followed where necessary by removal of any protecting groups.

According to one embodiment (a) of process (A), the reaction is effected with a compound of formula (III) wherein X represents the group —$CH_2L$, and L is preferably a halogen (e.g. chlorine) atom. The reaction may be carried out in an inert solvent such as an ether (e.g. dimethoxyethane, diglyme or tetrahydrofuran), a substituted amide (e.g. dimethylformamide or N-methylpyrrolidone), an aromatic hydrocarbon (e.g. toluene), a ketone (e.g. acetone), or dimethyl sulphoxide, at a temperature between ambient and 100° C., in the presence of a base. Suitable bases include alkali metal hydrides (e.g. sodium hydride), alkali metal carbonates (e.g. sodium carbonate), alkali metal amides (e.g. sodium amide), alkali metal alkoxides (e.g. potassium t-butoxide) or alkali metal hydroxides (e.g. sodium or potassium hydroxide).

According to another embodiment (b) of process (A), the reaction is effected with a compound of formula (III) wherein X represents the group —$CH_2OH$, in the presence of an acid. The acid may be, for example, a strong mineral acid (e.g. hydrochloric acid) or a hydrocarbylsulphonic acid (e.g. p-toluenesulphonic acid). The reaction may conveniently be effected in a high boiling polar solvent such as N-methylpyrrolidinone or dimethylacetamide, at an elevated temperature, for example in the range 100° to 200° C. Alternatively the reaction may be conveniently effected in water or an alcohol (e.g. isopropanol) at the reflux temperature of the solvent.

According to another general process (B), a compound of general formula (I) wherein Y represents the group $(CH_2)_n$ may be prepared by cyclising a compound of formula (IV):

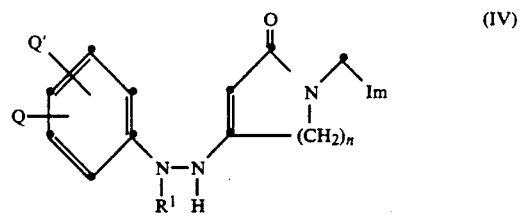

(IV)

or a salt or protected derivative thereof, followed where necessary by removal of any protecting groups.

It will be appreciated that these compounds of formula (IV) may exist in the corresponding enol hydrazone tautomeric form. The cyclisation may be carried out in aqueous or non-aqueous media, in the presence of an acid catalyst. When an aqueous medium is employed this may be water or a mixture of water and an organic solvent such as an alcohol (e.g. methanol, ethanol or isopropanol) or an ether (e.g. dioxan or tetrahydrofuran). The acid catalyst may be, for example, an inorganic acid such as concentrated hydrochloric or sulphuric acid. In some cases the acid catalyst may also act as the reaction solvent. In an anhydrous reaction medium, which may comprise one or more alcohols or ethers (e.g. as described above), carboxylic acids (e.g. acetic acid) or esters (e.g. ethyl acetate), the acid catalyst may alternatively be a Lewis acid such as boron trifluoride, zinc chloride or magnesium chloride. The cyclisation reaction may conveniently be carried out at temperatures of from 20° to 200° C., preferably 20° to 125° C.

Alternatively the cyclisation may be carried out in the presence of polyphosphate ester in a reaction medium which may comprise one or more organic solvents, preferably halogenated hydrocarbons such as chloroform, dichloromethane, dichloroethane, dichlorodifluoromethane, or mixtures thereof. Polyphosphate ester is a mixture of esters which may be prepared from phosphorus pentoxide, diethyl ether and chloroform according to the method described in 'Reagents for Organic Synthesis', (Fieser and Fieser, John Wiley and Sons, 1967).

According to another general process (C), a compound of general formula (I) wherein $R^3$ represents a hydrogen atom, may be prepared by the reaction of a compound of formula (V):

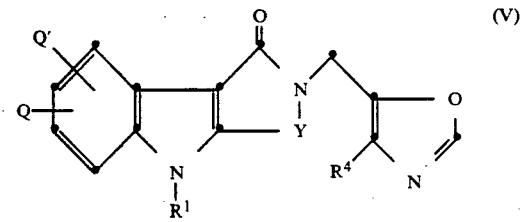

or a protected derivative thereof, with formamide, at a temperature in the range of 150° to 200° C., followed where necessary by removal of any protecting groups.

According to another general process (D), a compound of general formula (I) wherein Y represent the group $(CH_2)_n$ may be prepared by reacting a compound of formula (VI):

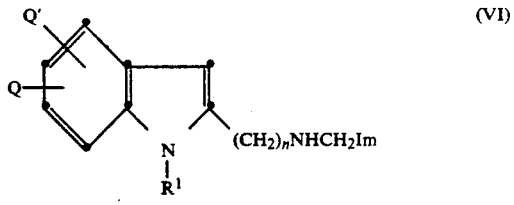

or a protected derivative thereof, with phosgene in the presence of a Lewis acid, followed where necessary by removal of any protecting groups.

The Lewis acid may be, for example, anhydrous aluminium trichloride or stannic chloride. The reaction may conveniently be effected in an inert solvent such as an aromatic hydrocarbon (e.g. toluene) or a halogenated hydrocarbon (e.g. dichloromethane), or mixtures thereof, and at a temperature between ambient and 100° C.

According to another general process (E), a compound of general formula (I) wherein Y represents the group $(CH_2)_n$ may be prepared by oxidising a compound of formula (VII):

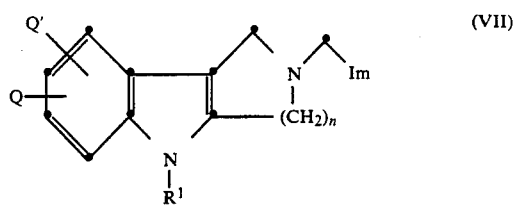

or a protected derivative thereof, followed where necessary by removal of any protecting groups.

The oxidation may be effected using conventional methods using an oxidising agent suitable for the conversion of the group $CH_2$ to the group $C=O$. Suitable oxidising agents include quinones (e.g. 2,3-dichloro-5,6-dicyano-1,4-benzoquinone), potassium permanganate in acetone, mercuric acetate and acetic acid, ruthenium tetraoxide or chromium trioxide in concentrated sulphuric acid.

Suitable solvents include ethers (e.g. tetrahydrofuran or dioxan), ketones (e.g. acetone), chlorinated hydrocarbons (e.g. chloroform), and water, or mixtures thereof. The process is conveniently effected at a temperature of $-70°$ to $+50°$. It will be understood that the choice of oxidising agent will affect the preferred reaction temperature.

According to another general process (F), a compound of general formula (I) may be converted into another compound of formula (I) using conventional techniques. Such conventional techniques include hydrogenation, alkylation and acylation using protection and deprotection where necessary.

Thus, according to one embodiment of the interconversion process (F), a compound of formula (I) wherein Y represents the group $(CH_2)_2$ may be prepared by hydrogenating the corresponding compound of formula (I) in which Y presents the group CH=CH. Hydrogenation may also be used to prepare a compound of formula (I) in which Q represents a hydroxyl group from the corresponding compound of formula (I) in which Q represents a phenylmethoxy group. Hydrogenation may also be used to convert an alkenyl or an alkynyl substituent into an alkyl substituent, or an alkynyl into an alkenyl substituent. Hydrogenation according to general process (F) may be effected using conventional procedures, for example, using hydrogen in the presence of a noble metal catalyst (e.g. palladium, Raney nickel, platinum or rhodium). The catalyst may be supported on, for example, charcoal or alumina, or alternatively a homogeneous catalyst such as tris(triphenylphosphine)rhodium chloride may be used. The hydrogenation will generally be effected in a solvent such as an alcohol (e.g. methanol or ethanol), an ether (e.g. dioxan), or an ester (e.g. ethyl acetate), or in a mixture of an alcohol and either a hydrocarbon (e.g. toluene) or a halogenated hydrocarbon (e.g. dichloromethane), at a temperature in the range $-20°$ to $+100°$ C., and at a pressure of from 1 to 10 atmospheres.

The term 'alkylation' according to general process (F) includes the introduction of groups such as cycloalkyl, alkenyl or phenalkyl groups.

Thus, for example, a compound of formula (I) in which $R^1$ represents a $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl or phenyl$C_{1-3}$alkyl group may be prepared by alkylating a compound of formula (I) in which $R^1$ represents a hydrogen atom, or a compound in which $R^3$ represents a $C_{1-6}$alkyl, $C_{3-7}$cycloalkyl, $C_{3-6}$alkenyl or phenyl$C_{1-3}$alkyl group may be prepared by alkylating the corresponding compound of formula (I) in which $R^3$ represents a hydrogen atom, using conventional procedures, for example as described in published European Patent Specification No. 242973. Thus the reactions may be effected using an appropriate alkylating agent of formula $R^{12}Z$ (where $R^{12}$ is the group to be introduced and Z is a leaving atom or group), preferably in the presence of a base.

According to another embodiment of general process (:F), a compound of formula (I) wherein $R^1$ represents $-CO_2R^5$, $-OR^5$, $-CONR^5R^6$ or $-SO_2R^5$ may be prepared by acylating or sulphonylating as appropriate, a compound of formula (I) wherein $R^1$ represents a hydrogen atom. The acylation/sulphonylation reactions may be effected using an appropriate acylating-/sulphonylating agent according to conventional procedures, for example, as described in published European Patent Specification No. 210840.

Compounds of formula (I) may also be prepared from other compounds of formula (I) by conventional functional group interconversion reactions, or by a series of such reactions.

Thus, for example, a compound of formula (I) wherein Q represents the group $-CONH_2$ may be prepared by reacting a compound of formula (I) in which Q represents a cyano group with a hydrolysing reagent suitable for the conversion of a cyano to an amido group. Suitable reagents include the hydroxide form of an anion exchange resin (e.g. Amberlite IRA 400 (OH)) and suitable solvents for this reaction include ethanol and water.

A compound of formula (I) wherein Q represents a group $-(CH_2)_2CO_2R^{11}$ may be prepared from a compound of formula (I) wherein Q represents a bromine atom, by reaction with a compound of formula $H_2C=CHCO_2H$ in the presence of an "arylpalladium" reagent which may be generated in situ, for example, by treating palladium acetate with tri-o-tolylphosphine in the presence of a base such as triethylamine. The reaction may conveniently be effected in a solvent such as acetonitrile and at an elevated temperature. The resulting carboxylic acid may be esterified using conventional methods, for example by reacting with the appropriate alcohol (e.g. methanol) and concentrated hydrochloric acid at an elevated temperature, and the propenoate so formed is then hydrogenated, for example, using hydrogen in the presence of a catalyst.

If required, a compound of formula (I) wherein Q represents a group $-(CH_2)_2CONR^7R^8$ may be prepared by reaction of a compound of formula (I) wherein Q represents a group $-(CH_2)_2CO_2R^{11}$ with the appropriate amine, $R^7R^8NH$.

It should be appreciated that in the above transformations it may be necessary or desirable to protect any sensitive groups in the molecule of the compound in question to avoid undesirable side reactions. For example, it may be necessary to protect the indole and/or imidazole nitrogen atoms, for example with an arylmethyl (e.g. trityl), arylmethoxymethyl (e.g. phenylmethoxymethyl), alkyl (e.g. t-butyl), alkoxymethyl (e.g. methoxymethyl), acyl (e.g. benzyloxycarbonyl) or a sulphonyl (e.g. N,N-dimethylaminosulphonyl or p-toluenesulphonyl) group. When Q represents a hydroxyl group it may be necessary to protect the hydroxyl group, for example with an arylmethyl (e.g. benzyl or trityl) group.

Thus according to another general process (G), a compound of general formula (I) may be prepared by the removal of any protecting groups from a protected form of a compound of formula (I). Deprotection may be effected using conventional techniques such as those described in 'Protective Groups in Organic Synthesis' by T. W. Greene (John Wiley and Sons, 1981).

For example, an arylmethoxymethyl N-protecting group may be cleaved by hydrogenolysis in the presence of a catalyst (e.g. palladium on charcoal). A trityl group may be cleaved by acid hydrolysis (e.g. using dilute hydrochloric or acetic acid). An alkoxyalkyl group may be removed using a mineral acid (e.g. dilute hydrochloric or hydrobromic acid). An acyl group may be removed by hydrolysis under acidic or basic conditions (e.g. using hydrogen bromide, dilute hydrochloric acid or sodium hydroxide). A sulphonyl group may also be removed by alkaline or acidic hydrolysis, and an N, N-dimethylaminosulphonyl group may also be removed (e.g. from an imidazole nitrogen atom) by photolysis. An arylmethyl OH-protecting group may be cleaved under acid conditions (e.g. with dilute acetic acid, hydrobromic acid or boron tribromide) or by hydrogenolysis in the presence of a catalyst (e.g. palladium on charcoal).

Compounds of formula (II) wherein Y represents the group $(CH_2)_n$ and $R^1$ represents a hydrogen atom may be prepared, for example, by the cyclisation of a compound of formula (VIII):

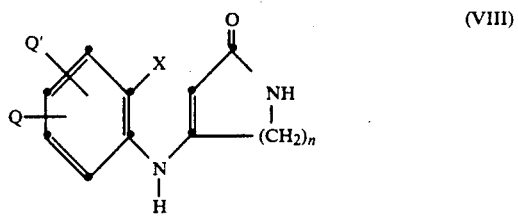

(VIII)

wherein X represents a hydrogen or a halogen (e.g. bromine or iodine) atom. The cyclisation may be effected using methods analogous to that described by H. Iida et al. in *J. Org. Chem.*, 1890, 45, 2938.

Compounds of formula (II) wherein Y represents the group $(CH_2)_n$ and $R^1$ represents a group other than a hydrogen atom may be prepared from a compound of formula (II) wherein $R^1$ represents a hydrogen atom by conventional alkylation, acylation and sulphonylation processes, as described, for example, in the interconversion process (F) above.

Compounds of formula (II) wherein Y represents the group CH=CH may be prepared by heating a compound of formula (II) wherein Y represents the group $(CH_2)_2$, or a protected derivative thereof, with a noble metal catalyst such as palladium, palladium oxide, platinum or nickel, at a temperature of, for example, 200° to 350° C. The catalyst may be supported on, for example, charcoal or alumina, and the reaction may optionally be carried out in the presence of an inert solvent such as an aromatic hydrocarbon (e.g. p-cymene) or ethylene glycol.

Compounds of formula (VIII) may be prepared, for example, by the reaction of a compound of formula (IX):

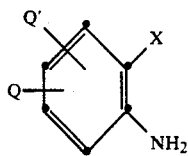

wherein X is as defined above, with a compound of formula (X):

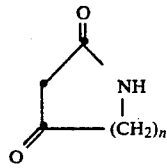

at an elevated temperature.

Compounds of formula (III) and protected derivatives thereof are either known or may be prepared, for example, by methods analogous to that described in published European Patent Specification No. 242973.

Compounds of formulae (IV), (V) and (VI) may be prepared for example, by methods analogous to those described in published European Patent Specification No. 306323a.

Compounds of formula (VII) may be prepared, for example, by the reaction of a compound of formula (XI):

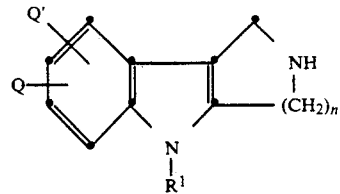

with a compound of formula (III), using the conditions described in embodiment (a) of process (A).

Compounds of formula (VII) may also be prepared by the reduction of a compound of formula (I), using a reducing agent suitable for the conversion of the group $C=O$ to the group $CH_2$, such as lithium aluminium hydride. The reaction may conveniently be effected in an inert solvent such as an ether (e.g. tetrahydrofuran) and at an elevated temperature.

Compounds of formulae (IX), (X) and (XI) are either known, or may be prepared from known compounds by conventional procedures.

Where it is desired to isolate a compound of the invention as a salt, for example a physiologically acceptable salt, this may be achieved by reacting the compound of formula (I) in the form of the free base with an appropriate acid, preferably with an equivalent amount, in a suitable solvent such as an alcohol (e.g. ethanol or methanol), an aqueous alcohol (e.g. aqueous ethanol), a halogenated hydrocarbon (e.g. dichloromethane), an ester (e.g. ethyl acetate) or an ether (e.g. tetrahydrofuran).

Physiologically acceptable salts may also be prepared from other salts, including other physiologically acceptable salts, of the compound of formula (I) using conventional methods.

Individual enantiomers of the compounds of the invention may be obtained by resolution of a mixture of enantiomers (e.g. a racemic mixture) using conventional means, such as an optically active resolving acid; see for example 'Stereochemistry of Carbon Compounds' by E. L. Eliel (McGraw Hill, 1962) and 'Tables of Resolving Agents' by S. H. Wilen.

The methods described above for preparing the compounds of the invention may be used for the introduction of the desired groups at any stage in the stepwise formation of the required compounds, and it will be appreciated that these methods can be combined in different ways in such multi-stage processes. The sequence of the reactions in multi-stage processes should of course be chosen so that the reaction conditions used do not affect groups in the molecule which are desired in the final product.

The invention is further illustrated by the following Intermediates and examples. All temperatures are in °C. Thin layer chromatography (t.l.c.) was carried out on silica, and flash column chromatography (FCC) on silica (Merck 9385). Solvent System A as used for chromatography denotes dichloromethane:ethanol:0.88 ammonia solution. Organic extracts were dried, where indicated, over magnesium sulphate or sodium sulphate. The following abbreviations are used; DMF—dimethylformamide; THF—tetrahydrofuran; DME—dimethoxyethane. $^1$H-N.m.r. spectra were obtained at 250 MHz for dilute solutions in $d_6$-dimethyl sulphoxide. The chloride form of Amberlite resin IRA 400 was obtained from B.D.H.

INTERMEDIATE 1

4-[(2-Fluorophenyl)amino]-5,6-dihydro-2(1$\underline{H}$)-pyridinone

A mixture of 2-fluoroaniline (0.98 g) and 2,4-dioxopiperidine (1.0 g) was heated at 120° for 2 h. The cooled mixture was triturated with dry ether (5×40 ml) and the solvent was decanted to leave the title compound (1.495 g), m.p. 98°–100°.

INTERMEDIATE 2

4-[(4-Fluorophenyl)amino]-5,6-dihydro-2(1$\underline{H}$)-pyridinone

A mixture of 4-fluoroaniline (978 mg) and 2,4-dioxopiperidine (1.0 g) was heated at 120° for 1 h, and then cooled. The solid was triturated with ether (30 ml) and the solvent was decanted to leave the title compound (1.71 g), m.p. 195°–198°.

INTERMEDIATE 3

5,6-Dihydro-4-[(2-methylphenyl)amino]-2(1$\underline{H}$)-pyridinone

A mixture of o-toluidine (943 mg) and 2,4-dioxopiperidine (1.0 g) was heated at 120° for 30 min. The oil was cooled, triturated with ether (30 ml) and the solvent was decanted to give the title compound (1.74 g), m.p. 155°–158°.

INTERMEDIATE 4

4-[(2,6-Dibromophenyl)amino]-5,6-dihydro-2(1$\underline{H}$)-pyridinone

A mixture of 2,6-dibromoaniline (4.4 g) and 2,4-dioxopiperidine (2.0 g) was heated at 120° for 2.5 h. The mixture was then cooled (0°) and triturated with ether 9100 ml) to give a solid which was purified by FCC

INTERMEDIATE 5

4-[(3-Fluorophenyl)amino]-5,6-dihydro-2(1H)-pyridinone

A mixture of 3-fluoroaniline (2 g) and 2,4-dioxopiperidine (2.04 g) was heated at 120° under nitrogen for 1 h. The resultant solid was cooled and purified by FCC eluting with System A (100:8:1) to give the title compound (2.49 g), m.p. 188°-190°.

INTERMEDIATE 6

4-[(2,5-Difluorophenyl)amino]-5,6-dihydro-2(1H)-pyridinone

A mixture of 2,5-difluoroaniline (6.45 g) and 2,4-dioxopiperidine (5.66 g) was heated under nitrogen for 6 h. The reaction mixture was then dissolved in ethanol (50 ml), adsorbed onto silica, and purified by FCC eluting with System A (150:8:1) to give the title compound (2.3 g), m.p. 252°-255°.

INTERMEDIATE 7

3-[(2-Fluorophenyl)amino]-2-cylcohexen-1-one

2-Fluoroaniline (10 g) and cyclohexane-1,3-dione (10 g) were heated together under nitrogen at 120° for 1 h. The cooled mixture was triturated with ether and filtered to give the title compound (14.8 g), m.p. 116°-118°.

INTERMEDIATE 8

6-Fluoro-2,3,4,5-tetrahydro-1H-pyrido[4,3-b]indol-1-one

Cupric acetate (2.71 g) was added to a stirred solution of 4-[(2-fluorophenyl)amino]-5,6-dihydro-2(1H)-pyridinone (1.4 g) and palladium (II) acetate (280 mg) in dry DMF (28 ml) under nitrogen. The mixture was heated at 130° for 1.5 h and the solvent was removed in vacuo. The residue was treated with hot methanol (50 ml) and the suspension was filtered and washed with hot methanol (3×50 ml). The combined filtrates were evaporated to give a gum (2.16 g) which was purified by FCC eluting with System A (200:10:1) to give the title compound (490 mg), m.p. 255°-257°.

INTERMEDIATE 9

8-Fluoro-2,3,4,5-tetrahydro-1H-pyrido[4,3-b]indol-1-one

Cupric acetate (2.9 g) was added to a stirred solution of 4-[(4-fluorophenyl)amino]-5,6-dihydro-2(1H)-pyridinone (1.5 g) and palladium (II) acetate (200 mg) in dry DMF (40 ml). The mixture was heated at 130° for 1 h, evaporated in vacuo and the residue was extracted with methanol (250 ml). This solution was concentrated in vacuo and the residue was purified by FCC eluting with System A (100:8:1) to give the title compound (840 mg), m.p. 242°-245°.

INTERMEDIATE 10

2,3,4,5-Tetrahydro-6-methyl-1H-pyrido[4,3-b]indol-1-one 5,6-Dihydro-4-[(2-methylphenyl)amino]-2(1H)-pyridinone (1.5 g) was cyclised according to the method of Intermediate 9 to give the title compound (360 mg), m.p. 300°-302°.

INTERMEDIATE 11

6-Bromo-2,3,4,5-tetrahydro-1H-pyrido[4,3-b]indol-1-one

4-[(2,6-Dibromophenyl)amino]-5,6-dihydro-2(1H)-pyridinone (0.5 g) was cyclised according to the method of Intermediate 9 to give the title compound (250 mg), m.p. 268°-270°.

INTERMEDIATE 12

7-Fluoro-2,3,4,5-tetrahydro-1H-pyrido[4,3-b]indol-1-one

4-[(3-Fluorophenyl)amino]-5,6-dihydro-2(1H)-pyridinone (2.3 g) was cyclised according to the method of Intermediate 9 to give the title compound (1.0 g), m.p. 213°-215°.

INTERMEDIATE 13

6,9-Difluoro-2,3,4,5-tetrahydro-1H-pyrido[4,3-b]indol-1-one

4-[(2,5-Difluorophenyl)amino]-5,6-dihydro-2(1H)-pyridinone (2.24 g) was cyclised according to the method of Intermediate 8 to give the title compound (900 mg), m.p. 221°-223°.

INTERMEDIATE 14

8-Fluoro-1,2,3,9-tetrahydro-4H-carbazol-4-one

3-[(2-Fluorophenyl)amino]-2-cylcohexen-1-one (14.8 g), palladium (II) acetate (1 g), and copper (II) acetate (29.5 g) were heated together in DMF (10 ml) under nitrogen at 140° for 2 h. The solvent was removed in vacuo, and the residue was purified by FCC eluting with ether to give the title compound (10.1 g), m.p. 222°-224°.

INTERMEDIATE 15

2,3,4,5-Tetrahydro-6-methoxy-1H-pyrido[4,3-b]indol-1-one

A mixture of 2-methoxyaniline (8.7 g) and 2,4-dioxopiperidine (8.0 g) was heated at 120° for 3 h. The mixture was then cooled and purified by FCC Eluting with System A (100:8:1) to give an oil (11 g). This oil was treated according to the method of Intermediate 14 (with the exception that System A (100:8:1) was used as the FCC eluant) to give the title compound (3.2 g), m.p. 255°-258°.

INTERMEDIATE 16

2,3,4,5-Tetrahydro-6-(phenylmethoxy)-1H-pyrido[4,3-b]indol-1-one

A mixture of 2-(phenylmethoxy)aniline (7.6 g) and 2,4-dioxopiperidine (4.5 g) was heated at 120° under nitrogen for 3 h. The mixture was then cooled and purified by FCC eluting with System A (100:8:1) to give a solid (5.4 g). This solid was treated according to the method of Intermediate 9 to give the title compound (4.0 g), m.p. 182°-185°.

INTERMEDIATE 17

6-Fluoro-2,3,4,5-tetrahydro-5-methyl-1H-pyrido[4,3-b]indol-1-one

Sodium hydride (60% dispersion in oil; 196 mg) was added to a stirred suspension of 6-fluoro-2,3,4,5-tetrahydro-1H-pyrido[4,3-b]indol-1-one (500 mg) in dry DMF (10 ml) under nitrogen. After 30 min the solution was cooled (0°), and methyl iodide (0.153 ml) was added. After stirring for 15 min the suspension was poured into water 950 ml) and extracted with dichloromethane (3×25 ml). The combined, dried organic extracts were evaporated to give a solid (ca. 530 mg) which was purified by FCC eluting with System A (250:10:1) to give the title compound (130 mg), m.p. 242°.

INTERMEDIATE 18

8-Fluoro-2,3,4,5-tetrahydro-5-methyl-1H-pyrido[4,3-b]indol-1-one

Sodium hydride (60% dispersion in oil; 196 mg) was added to a stirred solution of 8-fluoro-2,3,4,5-tetrahydro-1H-pyrido[4,3-b]indol-1-one (500 mg) in dry DMF (20 ml) at 21° under nitrogen. After 15 min, the solution was cooled (0°) and a 10% (v/v) solution of methyl iodide in DMF (1.6 ml) was added dropwise. After 10 min, water (150 ml) was added and the mixture was extracted with ethyl acetate (3×50 ml). The combined organic extracts were washed with water (3×50 ml), then brine (100 ml) and evaporated to give a solid which was purified by FCC Eluting with dichloromethane:-methanol (80:1) to give the title compound (240 mg), m.p. 200°-202°.

Intermediates 19 to 23 were prepared in a similar manner to Intermediate 18, i.e. by methylation of the appropriate 2,3,4,5-tetrahydro-1H-pyrido[4,3-b]indol-1-one using sodium hydride and methyl iodide in DMF.

INTERMEDIATE 19

2,3,4,5-Tetrahydro-5,6-dimethyl-1H-pyrido[4,3-b]indol-1-one

The methylation of 2,3,4,5-tetrahydro-6-methyl-1H-pyrido[4,3-b]indol-1-one (350 mg) gave the title compound (190 mg), m.p. 298°-300°.

INTERMEDIATE 20

6-Bromo-2,3,4,5-tetrahydro-5-methyl-1H-pyrido[4,3-b]indol-1-one

The methylation of 6-bromo-2,3,4,5-tetrahydro-1H-pyrido[4,3-b]indol-1-one (200 mg) gave the title compound (80 mg), m.p. 212°-214°.

INTERMEDIATE 21

7-Fluoro-2,3,4,5-tetrahydro-5-methyl-1H-pyrido[4,3-b]indol-1-one

The methylation of 7-fluoro-2,3,4,5-tetrahydro-1H-pyrido[4,3-b]indol-1-one (900 mg) gave the title compound (200 mg), m.p. 238°-240°. (The FCC eluant was System A (100:8:1)).

INTERMEDIATE 22

6,9-Difluoro-2,3,4,5-tetrahydro-5-methyl-1H-pyrido[4,3-b]indol-1-one

The methylation of 6,9-difluoro-2,3,4,5-tetrahydro-1H-pyrido[4,3-b]indol-1-one (900 mg) gave the title compound (110 mg), m.p. 226°-229°. (The FCC eluant was System A (150:8:1)).

INTERMEDIATE 23

2,3,4,5-Tetrahydro-6-methoxy-5-methyl-1H-pyrido[4,3-b]indol-1-one

The methylation of 2,3,4,5-tetrahydro-6-methoxy-1H-pyrido[4,3-b]indol-1-one (1.5 g) gave the title compound (680 mg), m.p. 242°-245°. (The FCC eluant was System A (100:8:1)).

INTERMEDIATE 24

8-Fluoro-1,2,3,9-tetrahydro-9-methyl-4H-carbazol-4-one

To a suspension of sodium hydride (80% dispersion in oil; 1.15 g) in dry THF (50 ml) under nitrogen was added 8-fluoro-1,2,3,9-tetrahydro-4H-carbazol-4-one (6.5 g) in dry THF (50 ml), and the mixture was stirred for 1 h. Methyl iodide (4.1 ml) was added, and the mixture was stirred for 3 h. The mixture was then poured into brine (300 ml) and extracted with ether (2×300 ml). The combined, dried organic extracts were evaporated in vacuo to give the title compound (5.77 g), m.p. 126°-128°.

INTERMEDIATE 25

2,3,4,5-Tetrahydro-5-methyl-6-(phenylmethoxy)-1H-pyrido[4,3-b]indol-1-one 2,3,4,5-Tetrahydro-6-(phenylmethoxy)-1H-pyrido[4,3-b]indol-1-one (2.0 g) was methylated according to the method of Intermediate 17 to give the title compound (950 mg), m.p. 199°-201°. (The FCC Eluant was System A (100:8:1)).

INTERMEDIATE 26

6-Fluoro-2,3,4,5-tetrahydro-5-[(phenylmethoxy)methyl]-1H-pyrido[4,3-b]indol-1-one 6-Fluoro-2,3,4,5-tetrahydro-1H-pyrido[4,3-b]indol-1-one (800 mg) was alkylated with benzylchloromethyl ether (0.55 ml) using the method of Intermediate 17 to give the title compound (220 mg), m.p. 130°-132°. (The FCC Eluant was System A (300:10:1)).

INTERMEDIATE 27

2,3,4,5-Tetrahydro-6-(phenylmethoxy)-5-[(phenylmethoxy)methyl]-1H-pyrido[4,3-b]indol-1-one 2,3,4,5-Tetrahydro-6-(phenylmethoxy)-1H-pyrido[4,3-b]indol-1-one (1.8 g) was alkylated with benzylchloromethyl ether (0.86 ml) using the method of Intermediate 18 to give the title compound (600 mg), m.p. 188°-190°. (The FCC eluant was System A (100:8:1)).

INTERMEDIATE 28

6-Fluoro-2,3,4,5-tetrahydro-5-(1-methylethyl)-1H-pyrido[4,3-b]indol-1-one

A stirred solution of 6-fluoro-2,3,4,5-tetrahydro-1H-pyrido[4,3-b]indol-1-one (1.006 g) in dry DMF (50 ml) was treated with sodium hydride (73.2% dispersion in oil; 333 mg) and stirred under nitrogen for 1 h. Isopropyl bromide (663 mg) was then added, and the solution was stirred at room temperature for 30 min and then at 50° for 12 h. A further portion of isopropyl bromide (150 mg) was then added, and the reaction was then stirred under nitrogen at 50° for ca. 60 h. The mixture was then cooled to room temperature and added to water 300 ml). The mixture was then extracted with dichloromethane (3×200 ml), adsorbed onto silica, and purified by FCC eluting with System A (150:8:1) to give a solid (240 mg) which was triturated with ether to give the title compound (130 mg), m.p. 183°-184°.

INTERMEDIATE 29

5-(Cyclopentylmethyl)-6-fluoro-2,3,4,5-tetrahydro-1H-pyrido[4,3-b]indol-1-one

A stirred solution of 6-fluoro-2,3,4,5-tetrahydro-1H-pyrido[4,3-b]indol-1-one (1.023 g) in dry DMF (50 ml) was treated with sodium hydride (73.2% dispersion in oil; 331 mg) and stirred under nitrogen at room temperature for 30 min. A solution of cyclopentylmethyl(-methyl sulphonate (893 mg) in dry DMF (20 ml) was then added over 15 min and stirring was continued for 5 days. Water (20 ml) was added to the reaction mixture which was then concentrated in vacuo to give a solid. This was dissolved in ethyl acetate (300 ml) and methanol (1 ml), and the resulting solution was washed with saturated sodium chloride solution (3 × 100 ml) and then adsorbed onto silica. Purification by FCC eluting with System A (150:8:1) gave a solid (283 mg) which was recrystallised from ethyl acetate to give the title compound (237 mg) m.p. 175°–176°.

INTERMEDIATE 30

8-Fluoro-1,2,3,9-tetrahydro-9-methyl-4H-carbazol-4-one oxime

A mixture of 8-fluoro-1,2,3,9-tetrahydro-9-methyl-4H-carbazol-4-one (3.0 g) and hydroxylamine hydrochloride (2.92 g) in pyridine (ca. 35 ml) was heated at 60° for 3 h. The solution was concentrated in vacuo then azeotropically dried with toluene (2 × 10 ml). The residue was treated with 8% sodium bicarbonate solution (125 ml) and extracted with ethyl acetate (3 × 100 ml). The combined extracts were filtered and concentrated in vacuo to give the title compound (1.8 g) as a solid, t.l.c. (System A, 100:8:1) Rf 0.66.

INTERMEDIATE 31

7-Fluoro-3,4,5,6-tetrahydro-6-methylazepino[4,3-b]indol-1(2H)-one

A mixture of 8-fluoro-1,2,3,9-tetrahydro-9-methyl-4H-carbazol-4-one oxime (1.8 g) and polyphosphoric acid (ca. 20 ml) in dioxan (30 ml) was stirred under nitrogen at 100°–110° for 1 h. After cooling, the reaction mixture was poured into iced water (1 l) and the resulting suspension was extracted with dichloromethane. The organic extract was concentrated in vacuo to give a solid which was taken up in methanol and adsorbed onto silica. Purification by FCC eluting with System A (200:8:1) gave the title compound (850 mg), m.p. 233°–235°.

INTERMEDIATE 32

2,3,4,5-Tetrahydro-5-methyl-1-oxo-1H-pyrido[4,3-b]indole-6-carbonitrile

A mixture of 6-bromo-2,3,4,5-tetrahydro-5-methyl-1H-pyrido[4,3-b]indol-1-one (1.1 g) and cuprous cyanide (1.0 g) in 1,3-dimethyl-3,4,5,6-tetrahydro-2(1H)-pyrimidone (30 ml) was heated at 180° for 24 h. The mixture was poured onto ice (ca. 500 ml) and ferric (III) chloride (20 g), and stirred for 1 h. It was then extracted with dichloromethane (3 × 300 ml), and the combined organic extracts were washed with water (2 × 300 ml) and concentrated in vacuo. The residue was triturated with hexane (250 ml) followed by a mixture of ether/hexane (50:50; 100 ml) and finally with ether (60 ml) to give the title compound (620 mg), m.p. 230°–231°.

INTERMEDIATE 33

2,3,4,5-Tetrahydro-5-methyl-6-phenyl-1H-pyrido[4,3-b]indol-1-one

A mixture of 6-bromo-2,3,4,5-tetrahydro-5-methyl-1H-pyrido[4,3-b]indol-1-one (200 mg), phenylboronic acid (131 mg), tetrakis(triphenylphosphine)palladium (0) (11 mg) and 2N sodium carbonate (5 ml) in DME (10 ml) was heated at reflux for 3 h. The cooled mixture was diluted with 2N sodium carbonate (50 ml) and extracted with dichloromethane (3 100 ml). The combined organic extracts were concentrated in vacuo and the residue was purified by FCC eluting with System A (100:8:1) to give a solid (180 mg) which was triturated with ether (20 ml) to give the title compound (160 mg), m.p. 242°–245°.

INTERMEDIATE 34

6-Fluoro-2,5-dihydro-5-methyl-1H-pyrido[4,3-b]indol-1-one

A mixture of 6-fluoro-2,3,4,5-tetrahydro-5-methyl-1H-pyrido[4,3-b]indol-1-one (300 mg) and 10% palladium oxide on carbon catalyst (50% aqueous paste; 150 mg) in ethylene glycol (30 ml) was heated at reflux under nitrogen for 24 h. The cooled mixture was filtered and evaporated to give a solid (ca. 300 mg) which was purified by FCC eluting with System A (200:10:1) to give a solid (100 mg). A sample of this solid was further purified by HPLC on a Spherisorb 55W column, eluting with System A (95:5:0.5) at a flow rate of 15 ml/min to give the title compound, m.p. 294°–296°.

INTERMEDIATE 35

6-Fluoro-2,3,4,5-tetrahydro-2-[(5-methyl-1H-imidazol-4-yl)methyl]-5-[(phenylmethoxy)methyl]-1H-pyrido[4,3-b]indol-1-one Sodium hydride (60% dispersion in oil; 28 mg) was added to a stirred solution of 6-fluoro-2,3,4,5-tetrahydro-5-[(phenylmethoxy)methyl]-1H-pyrido[4,3-b]indol-1-one (190 mg) in dry DME (10 ml). The mixture was heated at 50° for 6 h then treated with 4-(chloromethyl)-5-methyl-1-(triphenylmethyl)-1H-imidazole (261 mg) and stirring was continued under nitrogen for 18 h. Water (2 ml) and acetic acid (2 ml) were added and the solution was heated at reflux for 2.5 h. The solution was poured into 8% sodium bicarbonate solution (50 ml) and extracted with dichloromethane (3 × 25 ml). The combined, dried organic extracts were evaporated to give an oil (ca. 750 mg) which was purified by FCC eluting with System A (200:10:1) to give the title compound (188 mg), t.l.c (System A, 200:10:1) Rf 0.33.

INTERMEDIATE 36

6-Fluoro-2,3,4,5-tetrahydro-2-[[5-methyl-1-(triphenylmethyl-1H-imidazol-4-yl]methyl]-1H-pyrido[4,3-b]indol-1-one A solution of triphenylmethyl chloride (0.625 g) in dry DMF (10 ml) was added dropwise to a stirred solution of 6-fluoro-2,3,4,5-tetrahydro-2-[(5-methyl-1H-imidazol-4-yl)methyl]-1H-pyrido[4,3-b]indol-1-one (530 mg) in dry DMF (20 ml) containing triethylamine (0.25 g). The reaction mixture was then stirred at room temperature for 20 h, added to water (500 ml), and extracted with ethyl acetate (3 × 200 ml). The combined organic extracts were washed with water (2 × 300 ml), dried and adsorbed onto silica. Purification by FCC eluting with System A (150:8:1) gave the title compound (509 mg), m.p. 252°–253°.

INTERMEDIATE 37

2,3,4,5-Tetrahydro-2-[(5-methyl-1H-imidazol-4-yl)methyl]-6-(phenylmethoxy)-5-[(phenylmethoxy)methyl]-1H-pyrido[4,3-b]indol-1-one 2,3,4,5-Tetrahydro-6-(phenylmethoxy)-5-[(phenylmethoxy)methyl]-1H-pyrido[4,3-b]indol-1-one (500 mg) was reacted with 4-(chloromethyl)-5-methyl-1-(triphenylmethyl)-1H-imidazole (671 mg) according to the method of Intermediate 35 to give the title compound (340 mg), m.p. 170°–172°. (The FCC Eluant was System A (100:8:1)).

INTERMEDIATE 38

4-[(6-Bromo-2,3,4,5-tetrahydro-5-methyl-1-oxo-1H-pyrido[4,3-b]indol-2-yl)methyl]-N,N,5-trimethyl-1H-imidazole-1-sulphonamide Dimethylsulphamoyl chloride (0.31 ml) was added dropwise to a stirred suspension of 6-bromo-2,3,4,5-tetrahydro-5-methyl-2-[(5-methyl-1H-imidazol-4-yl) methyl]-1H-pyrido[4,3-b]indol-1-one (1.1 g) and triethylamine (0.48 ml) in dry dichloromethane (100 ml). The mixture was heated at reflux for 18 h, then a further quantity of triethylamine (0.48 ml) and dimethylsulphamoyl chloride (0.31 ml) was added. The solution was heated at reflux for 8 h then left at 21° for ca. 60 h. The solution was concentrated in vacuo and purified by FCC eluting with System A (100:8:1) to give a solid, which was triturated with hexane (50 ml) to give the title compound (500 mg), m.p. 182°–185°.

INTERMEDIATE 39

Methyl 3-[2,3,4,5-tetrahydro-5-methyl-2-[(5-methyl-1H-imidazol-4-yl)methyl]-1-oxo-1H-pyrido[4,3-b]indol-6-yl]-2-propenoate A mixture of 4-[(6-bromo-2,3,4,5-tetrahydro-5-methyl-1-oxo-1-oxo-1H-pyrido [4,3-b]indol-2-yl)methyl]-N,N,5-trimethyl-1H-imidazole-1-sulphonamide (500 mg) acrylic acid (0.08 ml), palladium acetate (27 mg) and tri-o-tolylphosphine (54 mg) in triethylamine (0.27 ml) and acetonitrile (7 ml) was heated at 80°–90° for 18 h in a closed vessel. A further quantity of palladium acetate (27 mg) and triethylamine (0.27 ml) were added and the mixture was heated for 6 h then concentrated in vacuo. The residue was treated with 2N sodium hydroxide (30 ml), washed with ether (3×30 ml) and the aqueous phase (plus oily residue) was then acidified (to pH1) with 5N hydrochloric acid. The aqueous phase was extracted with dichloromethane:methanol (10:1; 3×150 ml) and the combined organic extracts were concentrated in vacuo. Methanol (100 ml) was added to the residue, followed by concentrated hydrochloric acid (0.15 ml), and the mixture was heated at reflux for 5 h. The mixture was then concentrated in vacuo and the residue was basified (to pH9) with 8% sodium bicarbonate solution. The mixture was filtered and the solid was washed with water (ca. 100 ml) and dried at 60° in vacuo to give the title compound (230 mg), m.p. 175°–178°.

INTERMEDIATE 40

4-Amino-5,6-dihydro-1-[(5-methyl-1H-imidazol-4-yl)methyl]-2(1H) -pyridinone

To a solution of 5,6-dihydro-4-methoxy-1-[(5-methyl-1H-imidazol-4-yl)methyl]-2(1H)-pyridinone (1.00 g) in THF (10 ml) was added hydrochloric acid (4.3 ml), and the mixture was stirred at 25° for 24 h. The solvent was removed in vacuo. The residue was dissolved in methanol (10 ml), adsorbed onto silica, and purified by FCC eluting with System A (50:8:1) to give the title compound (286 mg) as a solid, m.p. 268°–271°.

INTERMEDIATE 41

4-[2-(2-Fluorophenyl)-2-methylhydrazine]-5,6-dihydro-1-[(5-methyl-1H-imidazol-4-yl)methyl]-2(1H)-pyridinone A mixture of 1-(2-fluorophenyl)-1-methylhydrazine (57 mg) and 4-amino-5,6-dihydro-1-[(5-methyl-1H-imidazol-4-yl)methyl]-2(1H) -pyridinone (70 mg) in absolute ethanol (3 ml) was stirred at room temperature for 4 h then at reflux for 20 h. The solvent was removed in vacuo and the residue was purified by FCC eluting with System A (75:10:1) to give the title compound (85 mg) as an oil, t.l.c. (System A, 200:10:1) Rf 0.27.

INTERMEDIATE 42

6-Fluoro-2,3,4,5-tetrahydro-5-methyl-2-[(4-methyloxazol-5-yl)methyl]-1H-pyrido[4,3-b]indol-1-one Sodium hydride (73% dispersion in oil; 167 mg) was added to a stirred suspension of 6-fluoro-2,3,4,5-tetrahydro-5-methyl-1H-pyrido[4,3-b]indol-1-one (500 mg) in dry DME (150 ml), and the suspension was stirred at 60° under nitrogen for 6 h. 5-Chloromethyl-4-methyloxazole (440 mg) was then added and the mixture was stirred overnight at 60°. A further quantity of sodium hydride (73% dispersion in oil; 84 mg) was added and the mixture was stirred for 3 h, and then cooled (0°). Water (200 ml) was added, and the mixture was extracted with dichloromethane (3×200 ml). The combined organic extracts were concentrated in vacuo and the residue was purified by FCC eluting with System A (100:8:1) to give the title compound (550 mg) as a solid, m.p. 158°–161°.

INTERMEDIATE 43

Ethyl 7-fluoro-1-methyl-1H-indole-2-carboxylate

To a suspension of sodium hydride (73.2% dispersion in oil; 962 mg) in dry THF (50 ml) under nitrogen at 0° was added ethyl 7-fluoro-1H-indole-2-carboxylate (5.5 g) in dry THF (50 ml), and the mixture was stirred for 1 h. Methyl iodide (2.16 ml) was added, and the mixture was stirred for 2 h, then at 50° for 3 h. The mixture was quenched with 10% aqueous THF (5 ml), diluted with ether (500 ml), washed with saturated brine solution (2×500 ml), dried and evaporated in vacuo to leave an oil. This was purified by FCC eluting with hexane:ether (20:1) to give the title compound (4.53 g) as a liquid, t.l.c. (hexane:ether, 20:1) Rf 0.37.

INTERMEDIATE 44

7-Fluoro-1-methyl-1H-indole-2-methanol

Ethyl 7-fluoro-1-methyl-1H-indole-2-carboxylate (4.5 g) was dissolved in dry THF (50 ml), and cooled to −78° under nitrogen. Diisobutylaluminium hydride (DIBAL) (1M solution in hexane; 22.3 ml) was added and the mixture was stirred at −78° for 3 h, then allowed to warm to room temperature over 1 h. A further portion of DIBAL :(3 ml) was added to the recooled mixture at −78°, and stirring was continued for a further 16 h. Saturated ammonium chloride solution (10 ml) was added and the mixture was stirred for 30 min. Magnesium sulphate (dried, 10 g) was added, and the resultant mixture was filtered and evaporated in vacuo to leave an oil which was purified by FCC eluting with ether:hexane (1:1) to give the title compound (1.55 g) as a solid, m.p. 89°–91°.

INTERMEDIATE 45

7-Fluoro-1-methyl-1H-indole-2-carboxaldehyde

7-Fluoro-1-methyl-1H-indole-2-methanol (2.0 g) was dissolved in 1,4-dioxan (50 ml). Manganese dioxide (2.91 g) was added and the mixture was heated at reflux for 1 h. The mixture was then filtered and the filtrate was evaporated in vacuo to give the title compound (1.77 g) as a solid, m.p. 61°–63°.

INTERMEDIATE 46

(E)-7-Fluoro-1-methyl-2-(2-nitroethenyl)-1H-indole

To a solution of 7-fluoro-1-methyl-1H-indole-2-carboxaldehyde (1.80 g) in nitromethane (20 ml) was added ammonium acetate (780 mg) and the mixture was heated at reflux for 1 h. The solvent was removed in vacuo and the residue was suspended in ethyl acetate (300 ml). This suspension was washed with 8% aqueous sodium bicarbonate solution (2×300 ml), dried, and the solvent was removed in vacuo to leave the title compound (1.26 g) as a solid, m.p. 153°–155.5°.

INTERMEDIATE 47

2,2,2-Trifluoro-N-[2-(7-fluoro-1-methyl-1H-indol-2-yl)ethyl]acetamide (E)-7-Fluoro-1-methyl-2-(2-nitroethenyl)-1H-indole (1.2 g) in dry THF (40 ml) was added slowly to a stirred suspension of lithium aluminium hydride (1.0 g) in dry THF (40 ml) under nitrogen and the mixture was stirred overnight at room temperature. Another portion of lithium aluminium hydride (200 mg) was added, and the mixture was stirred for a further 18 h. 10 % Aqueous THF (10 ml) was added slowly and the mixture was stirred for 30 min. Magnesium sulphate (20 g) was added, the mixture was filtered, and the filter cake was washed with ethyl acetate (100 ml). The combined filtrates were evaporated in vacuo to leave a gum which was dissolved in dichloromethane (100 ml). Triethylamine (5 ml) was added, and the mixture was cooled to 0°. Trifluoroacetic anhydride (1 ml) was added dropwise and the resulting mixture was stirred for 1 h. The mixture was diluted with dichloromethane (100 ml), washed with 8% aqueous sodium bicarbonate solution (2×100 ml), dried and the solvent removed in vacuo to leave a gum. This was purified by FCC eluting with hexane:ether (2:1) to give the title compound (293 mg) as a solid, m.p. 108.5°–109.5°.

INTERMEDIATE 48

N[[1-[(Dimethylamino)sulphonyl]-5-methyl-1H-imidazol-4-yl]methyl]-2,2,2-trifluoro-N -[2-(7-fluoro-1-methyl-1H-indol-2-yl)ethyl]acetamide 2,2,2-Trifluoro-N-[2-(7-fluoro-1-methyl-1H-indol-2-yl)ethyl]acetamide (263.5 mg) in dry DME (5 ml) was added to a suspension of sodium hydride (73.2% dispersion in oil; 33 mg) in dry DME (4 ml) under nitrogen, and the mixture was stirred at 50° for 1 h. 4-(Chloromethyl)-N,N-5-trimethyl-1H-imidazole-1-sulphonamide (239 mg) in dry DME (5 ml) was then added, and the mixture was stirred at 50° overnight. The mixture was then diluted with ethyl acetate (100 ml), washed with brine (100 ml), dried and evaporated in vacuo to leave an oil. This was purified by FCC eluting with ethyl acetate:ether (1:1) to give the title compound (243 mg) as a foam, m.p. 43°–45°.

INTERMEDIATE 49

4-[[[2-(7-Fluoro-1-methyl-1H-indol-2-yl)ethyl]amino]methyl]-N,N,5-trimethyl -1H-imidazole-1-sulphonamide To a solution of N-[[1-[(dimethylamino)sulphonyl]-5-methyl-1H-imidazol -4-yl]methyl]-2,2,2-trifluoro-N-[2-(7-fluoro-1-methyl-1H-indol-2-yl)-ethyl]acetamide (230 mg) in methanol (10 ml) was added potassium carbonate (350 mg), and the mixture was heated at reflux for 2 h. The mixture was then diluted with ethyl acetate (100 ml), washed with 8% sodium bicarbonate solution (100 ml), dried, and evaporated in vacuo to leave an oil. This was purified by FCC eluting with System A (200:8:1) to give the title compound (110 mg) as a solid, m.p. 114°–115.5°.

INTERMEDIATE 50

4-[(6-Fluoro-2,3,4,5-tetrahydro-5-methyl-1-oxo-1H-pyrido[4,3-b]indol-2-yl) methyl]-N,N,5-trimethyl-1H-imidazole-1-sulphonamide To a stirred solution of phosgene (12.5% v/v in toluene; 4 ml) in dichloromethane (4 ml) was added a solution of 4-[[[2-(7-fluoro-1-methyl-1H-indol-2-yl)ethyl]amino]methyl]-N,N,5-trimethyl-1H-imidazole-1-sulphonamide (100 mg) in dichloromethane (4 ml), and the resulting mixture was stirred for 1 h. The solvent was removed in vacuo, and the residue was dissolved in dichloromethane (5 ml). Aluminium chloride (68 mg) was added, and the mixture was heated at reflux for 3 h. The cooled mixture was then poured into 2M sodium hydroxide solution (80 ml) and extracted with dichloromethane (2×50 ml). The combined, dried organic extracts were evaporated in vacuo to leave a solid which was dissolved in dichloromethane:methanol (1:1; 50 ml) and adsorbed onto silica. Purification by FCC eluting with System A (200:8:1) gave a solid (21 mg) which was triturated with ether to give the title compound (14 mg), m.p. 162°–166°.

INTERMEDIATE 51

6-Fluoro-2,3,4,5-tetrahydro-5-methyl-2-[(5-methyl-1H-imidazol-4-yl)methyl]-1H-pyrido[4,3-b]indole A stirred solution of 6-fluoro-2,3,4,5-tetrahydro-5-methyl-2-[(5-methyl -1H-imidazol-4-yl)methyl]-1H-pyrido[4,3-b]indol-1-one (277 mg) in dry THF (75 ml) was treated portionwise with lithium aluminium hydride (67 mg) under nitrogen, and the suspension was then heated at reflux for 2 h. After cooling, water (10 ml) was added dropwise followed by sodium sulphate, and the mixture was then filtered. The filtrate was adsorbed onto silica and purified by FCC eluting with System A (100:8:1) to give the title compound (196 mg) as a solid, m.p. 188.5°–189.5°.

INTERMEDIATE 52

6-Fluoro-2,3,4,5-tetrahydro-2-[[1-(methoxymethyl)-5-methyl-1H-imidazol-4-yl]methyl]-5-methyl-1H-pyrido[4,3-b]indol-1-one and
6-Fluoro-2,3,4,5-tetrahydro-2-[[1-(methoxymethyl)-4-methyl-1H-imidazol-5-yl]methyl]-5-methyl-1H-pyrido[4,3-b]indol-1-one A stirred solution of 6-fluoro-2,3,4,5-tetrahydro-5-methyl-2-[(5-methyl -1H-imidazol-4-yl)methyl]-1H-pyrido[4,3-b]indol-1-one maleate (728 mg) and triethylamine (0.52 ml) in dichloromethane (50 ml) was treated with a solution of chloromethyl methyl ether (0.27 ml) in dichloromethane (20 ml), and the mixture was stirred at 20° under nitrogen for 2½ days. The reaction mixture was then added to water (50 ml) and sodium hydroxide (100 ml) and extracted with dichloromethane (2×75 ml). The combined, dried organic extracts were adsorbed onto silica, and purified by FCC eluting with System A (150:8:1) to give an oil. This oil was triturated with ether to give the title compounds (60 mg) as a solid, t.l.c. (System A, 100:8:1) Rf 0.32.

INTERMEDIATE 53

Phenylmethyl
4-[(6-fluoro-2,3,4,5-tetrahydro-5-methyl-1-oxo-1H-pyrido
[4,3-b]indol-2-yl)methyl]-5-methyl-1H-imidazole-1-carboxylate A solution of benzyl chloroformate (0.47 ml) in dichloromethane (1 ml) was added to a stirred solution of 6-fluoro-2,3,4,5-tetrahydro-5-methyl-2-[(5-methyl -1H-imidazol-4-yl)methyl]-1H-pyrido[4,3-b]indol-1-one (496 mg) and triethylamine (0.67 ml) in dry dichloromethane (50 ml) at 20° under nitrogen, and the mixture was stirred overnight. The cooled reaction mixture was then added to 2N sodium hydroxide (100 ml) and extracted with dichloromethane (2×100 ml). The combined, dried organic extracts were adsorbed onto silica and purified by FCC eluting with System A (200:8:1) to give the title compound (442 mg) as a solid. A sample was recrystallised from hot ethyl acetate, and the resultant solid was triturated with ether to give a crystalline solid, m.p. 126°-128°.

EXAMPLE 1

6-Fluoro-2,3,4,5-tetrahydro-5-methyl-2-[(5-methyl-1H-imidazol-4-yl) methyl]-1H-pyrido[4,3-b]indol-1-one maleate Sodium hydride (60% dispersion in oil; 25 mg) was added to a stirred suspension of 6-fluoro-2,3,4,5-tetrahydro-5-methyl-1H-pyrido[4,3-b]indol-1-one (115 mg) in dry DME (7.5 ml) under nitrogen. The mixture was heated at 50° for 6 h then treated with 4-(chloromethyl)-5-methyl-1-(triphenylmethyl) -1H-imidazole (236 mg), and stirring was continued at 50° for 18 h. Water (1.25 ml) and acetic acid (1.25 ml) were added and the solution was heated at reflux for 6 h. The mixture was poured into 8% sodium bicarbonate solution (40 ml) and extracted with dichloromethane (3×20 ml). The combined, dried organic extracts were evaporated to give a solid (375 mg) which was purified by FCC eluting with System A (200:10:1) to give the free base of the title compound as a solid (147 mg). This was dissolved in dichloromethane (3 ml) and treated with a solution of maleic acid (55 mg) in absolute ethanol (0.5 ml). The solvent was removed in vacuo and the residue was triturated with dry ether (3×5 ml) to give the title compound (185 mg), m.p. 178°-180°.

Analysis Found: C,59.0; H,5.0; N,12.85; $C_{17}H_{17}FN_4O \cdot C_4H_4O_4$ requires C,58.9; H,4.9; N,13.1%.

Examples 2 to 13 were prepared in a similar manner to Example 1, i.e. by reacting the appropriate lactam with 4-(chloromethyl)-5-methyl-1-(triphenylmethyl)-1H-imidazole (hereinafter referred to as Compound X) in DME in the presence of sodium hydride. Deprotection was effected with acetic acid and water (followed by 2N hydrochloric acid in the case of Example 8), and subsequent basification of the solution was then effected with 2N sodium hydroxide solution rather than 8% sodium bicarbonate solution. The basic solution was then extracted with dichloromethane (or ethyl acetate in the case of Examples 6 and 12), and the combined, dried organic extracts were evaporated in vacuo. Purification of the residue was by FCC eluting with System A [Ex. 2 (160:8:1), Exs. 3,6,7,12,13 (150:8:1) and Exs. 4,5,8,9,10,11 (100:8:1)] to give the free base of the title compound. Maleate formation was as described in Example 1 except that methanol was used (instead of ethanol) as the recrystallisation solvent, and the mixture was heated on a steam bath for 10 min. The product was obtained from this methanolic solution either by evaporation to dryness in vacuo, and subsequent trituration of the resultant residue with ether (Exs. 4,5,8,9,11) or recrystallisation of the residue from a mixture of methanol and ether (Ex. 10), or the product was precipitated from the methanolic solution by the addition of ether (Exs. 2,3,6,7,12,13). The products of Examples 2 and 11 were further purified as described below.

EXAMPLE 2

8-Fluoro-2,3,4,5-tetrahydro-5-methyl-2-[(5-methyl-1H-imidazol-4-yl) methyl]-1H-pyrido[4,3-b]indol-1-one maleate The reaction of 8-fluoro-2,3,4,5-tetrahydro-5-methyl-1H-pyrido[4,3-b]indol-1-one (200 mg) with compound X (371 mg) gave the free base of the title compound (210 mg). Maleate formation gave a solid (190 mg) which was recrystallized from methanol/ether to give a solid (85 mg), a portion of which (78 mg) was reconverted to the free base by addition of 2N sodium hydroxide (10 ml) and extraction into dichloromethane (3×10 ml). The combined, dried organic extracts were concentrated in vacuo to give the free base (70 mg) which was purified by HPLC (Zorbax 5-6 μm silica, 250×9.4 mm column) eluting with hexane: chloroform: ethanol: 0.88 ammonia solution (40:100:20:0.2) to give a solid (40 mg). This was treated with maleic acid (15 mg) in methanol on a steam bath for 10 min. The solution was concentrated in vacuo and the residue was triturated with ether (15 ml) to give the title compound (45 mg), m.p. 145°.

$^1$H-N.m.r. δ2.35 (3H,s), 3.12 (2H,t), 3.68 (2H,t), 3.75 (3H,s), 4.67 (2H,brs), 6.08 (2H,s), 7.085 (1H,ddd), 7.53-7.655 (2H,m), 8.83 (1H, brs).

EXAMPLE 3

2,3,4,5-Tetrahydro-5,6-dimethyl-2-[(5-methyl-1H-imidazol-4-yl)methyl]-1H-pyrido[4,3-b]indol-1-one maleate The reaction of 2,3,4,5-tetrahydro-5,6-dimethyl-1H-pyrido[4,3-b]indol-1-one (150 mg) with Compound X (260 mg) gave the free base of the title compound (120 mg). Maleate formation gave the title compound (110 mg), t.l.c. (System A, 150:8:1) Rf 0.3.

$^1$H-N.m.r. δ2.35 (3H,s), 2.75 (3H,s), 3.08 (2H,t), 3.64 (2H,t), 3.93 (3H,s), 4.62 (2H,s), 6.07 (2H,s), 6.90 (1H,brd), 7.01 (1H,t), 7.88 (1H,brd), 8.73 (1H,brs).

EXAMPLE 4

6-Bromo-2,3,4,5-tetrahydro-5-methyl-2-[(5-methyl-1H-imidazol-4-yl)methyl]-1H-pyrido[4,3-b]indol-1-one maleate The reaction of 6-bromo-2,3,4,5-tetrahydro-5-methyl-1H-pyrido[4,3-b]indol-1-one (140 mg) with Compound X (280 mg) gave the free base of the title compound (130 mg). Maleate formation gave the title compound (170 mg), m.p. 155°.

Water Analysis Found 2.86% w/w≡0.79 mol H$_2$O.
Analysis: Found: C,50.1; H,4.4; N,10.7;
C$_{17}$H$_{17}$BrN$_4$O.C$_4$H$_4$O$_4$.0.79H$_2$O requires C,50.1; H,4.5; N,11.1%.

EXAMPLE 5

7-Fluoro-2,3,4,5-tetrahydro-5-methyl-2-[(5-methyl-1H-imidazol-4-yl)methyl]-1H-pyrido[4,3-b]indol-1-one maleate The reaction of 7-fluoro-2,3,4,5-tetrahydro-5-methyl-1H-pyrido[4,3-b]indol-1-one (150 mg) with Compound X (386 mg) gave the free base of the title compound (200 mg). Maleate formation gave the title compound (200 mg), m.p. 150°.

$^1$H-N.m.r. δ2.36(3H,s), 3.11(2H,t), 3.67(2H,t), 3.72(3H,s), 4.66(2H,s), 6.08(2H,s), 7.04(1H,m), 7.47(1H,dd), 7.92(1H,dd), 8.87(1H,s).

EXAMPLE 6

6,9-Difluoro-2,3,4,5-tetrahydro-5-methyl-2-[(5-methyl-1H-imidazol-4-yl)methyl]-1H-pyrido[4,3-b]indol-1-one maleate The reaction of 6,9-difluoro-2,3,4,5-tetrahydro-5-methyl-1H-pyrido [4,3-b]indol-1-one (1.0 g) with Compound X (1.7 g) gave the free base of the title compound (846 mg). Maleate formation gave the title compound (920 mg), m.p. 206°-208°.

Analysis Found: C,56.1; H,4.6; N,12.6;
C$_{17}$H$_{16}$N$_4$O.C$_4$H$_4$O$_4$ requires C,56.5; H,4.5; H,12.6%.

EXAMPLE 7

7-Fluoro-3,4,5,6-tetrahydro-6-methyl-2-[(5-methyl-1H-imidazol-4-yl)methyl]-azepino[4,3-b]indol-1(2H)-one maleate The reaction of 7-fluoro-3,4,5,6-tetrahydro-6-methylazepino[4,3-b]indol-1(2H)-one (850 mg) with Compound X (1.64 g) gave the free base of the title compound (358 mg). Maleate formation gave the title compound (383 mg) m.p. 143°-145°.

Water Analysis Found: 1.19% w/w≡0.296 mol H$_2$O.
Analysis Found: C,59.2; H,5.6; N,12.5;
C$_{18}$H$_{19}$N$_4$OF.C$_4$H$_4$O$_4$.0.296H$_2$O requires C,59.0; H,5.3; N,12.5%.

EXAMPLE 8

2,3,4,5-Tetrahydro-6-methoxy-5-methyl-2-[(5-methyl-1H-imidazol-4-yl)methyl]-1H-pyrido[4,3-b]indol-1-one maleate The reaction of 2,3,4,5-tetrahydro-6-methoxy-5-methyl-1H-pyrido[4,3-b]indol-1-one (600 mg) with Compound X (1.46 g) gave the free base of the title compound (600 mg). A portion of the free base (200 mg) was treated with maleic acid to give the title compound (250 mg), m.p. 158°.

Water Analysis Found: 1.64% w/w≡0.4 mol H$_2$O.
Analysis Found: C,58.9; H,5.6; N,12.3;
C$_{18}$H$_{20}$N$_4$O$_2$.C$_4$H$_4$O$_4$.0.4H$_2$O requires C,58.9; H,5.5; N,12.5%.

EXAMPLE 9

2,3,4,5-Tetrahydro-5-methyl-2-[(5-methyl-1H-imidazol-4-yl)methyl]-6-(phenylmethoxy)-1H-pyrido[4,3-b]indol-1-one maleate The reaction of 2,3,4,5-tetrahydro-5-methyl-1H-pyrido[4,3-b]indol-1-one (900 mg) with Compound X (1.6 g) gave the free base of the title compound (800 mg). A portion of the free base (90 mg) was treated with maleic acid to give the title compound (90 mg), m.p. 158°-160°. T.l.c. (System A, 100:8:1) Rf 0.2.

EXAMPLE 10

2,3,4,5-Tetrahydro-5-methyl-2-[(5-methyl-1H-imidazol-4-yl)methyl]1-oxo-1H-pyrido[4,3-b]indole-6-carbonitrile maleate The reaction of 2,3,4,5-tetrahydro-5-methyl-1-oxo-1H-pyrido[4,3-b]indole-6-carbonitrile (550 mg) with Compound X (1.3 g) gave the free base of the title compound (410 mg). A portion of the free base (100 mg) was treated with maleic acid to give the title compound (50 mg), t.l.c. (System A, 100:8:1) Rf 0.2.

Analysis Found: C,60.4; H,4.8; N,15.6;
C$_{18}$H$_{17}$N$_5$O.C$_4$H$_4$O$_4$: C,60.7; H,4.9; N,16.0%.

EXAMPLE 11

2,3,4,5-Tetrahydro-5-methyl-2-[(5-methyl-1H-imidazol-4-y-l)methyl]-6-phenyl-1H-pyrido[4,3-b]indol-1-one maleate The reaction of 2,3,4,5-tetrahydro-5-methyl-6-phenyl-1H-pyrido[4,3-b]indol-1-one (100 mg) with Compound X (193 mg) gave the free base of the title compound (120 mg). Maleate formation gave a solid (150 mg) which was purified by HPLC (Spherisorb 55W, 25 cm×20 mm column) eluting with chloroform: hexane: ethanol: 0.88 ammonia (100:50:10:0.1) at a flow rate of 20 ml/min to give the free base of the title compound (49 mg). This was reconverted to the maleate by the method used in Example 4 to give the title compound (53 mg), m.p. 215°.

$^1$H-N.m.r.δ 2.37 (3H,s), 3.07 (2H,t), 3.17 (3H,s), 3.67 (2H,t), 4.67 (2H,s), 6.10 (2H,s), 6.98 (1H,dd), 7.22 (1H,t), 7.4-7.55 (5H,m), 8.07 (1H,brd), 8.92 (1H,s).

EXAMPLE 12

6-Fluoro-2,3,4,5-tetrahydro-5-(1-methylethyl)-2-[(5-methyl-1H-imidazol-4-yl) methyl]-1H-pyrido[4,3-b]indol-1-one maleate The reaction of 6-fluoro-2,3,4,5-tetrahydro-5-(1-methylethyl)-1H-pyrido [4,3-b]indol-1-one (130 mg) with Compound X (295 mg) gave the free base of the title compound (69 mg). A portion of the free base (66 mg) was treated with maleic acid to give the title compound (79 mg), m.p. 185°-187°.

Analysis: Found: C,60.2; H, 5.6; N, 12.0;
C$_{19}$H$_{21}$FN$_4$O.C$_4$H$_4$O$_4$ requires C,60.5; H, 5.5; N, 12.3%.

EXAMPLE 13

5-(Cyclopentylmethyl)-5-fluoro-2,3,4,5-tetrahydro-2-[(5-methyl-1H-imidazol-4-yl) methyl]-1H-pyrido[4,3-b]indol-1-one maleate The reaction of 5-(cyclopentylmethyl)-5-fluoro-2,3,4,5-tetrahydro-1H-pyrido [4,3-b]indol-1-one (222 mg) with Compound X (317 mg) gave the free base of the title compound (100 mg). Maleate formation gave the title compound (85 mg), m.p. 164°–166°.

Analysis: Found: C, 62.5; H, 5.9; N, 11.0;
$C_{22}H_{25}FN_4O.C_4H_4O_4$ requires C, 62.9; H, 5.9; N, 11.3%.

EXAMPLE 14

6-Fluoro-2,5-dihydro-5-methyl-2-[(5-methyl-1H-imidazol-4-yl)methyl]-1H-pyrido[4,3-b]indol-1-one maleate 6-Fluoro-2,5-dihydro-5-methyl-1H-pyrido[4,3-b]indol-1-one (140 mg) was reacted with Compound X (290 mg) according to the method of Example 1 to give the free base of the title compound (143 mg). This material was dissolved in dichloromethane:ethanol (1:1; 20 ml) and treated with a solution of maleic acid (56 mg) in ethanol (2 ml). The solvent was removed in vacuo to leave a solid which was crystallised from ethyl acetate/methanol to give the title compound (75 mg), m.p. 183°–184°.

Analysis: Found: C,59.2; H,4.3; N,12.9;
$C_{17}H_{15}FN_4O.C_4H_4O_4$ requires C,59.2; H, 4.5; N,13.1%.

EXAMPLE 15

6-Fluoro-2,3,4,5-tetrahydro-5-methyl-2-[(5-propyl-1H-imidazol-4-yl) methyl]-1H-pyrido[4,3-b]indol-1-one maleate Sodium hydride (73% dispersion in oil; 66 mg); was added to a stirred suspension of 6-fluoro-2,3,4,5-tetrahydro-5-methyl-1H-pyrido [4,3-b]indol-1-one (289 mg) in dry DME (30 ml), and the mixture was heated at 60° under nitrogen for 6 h. 4-(Chloromethyl)-N,N-dimethyl-5-propyl-1H-imidazol -1-sulphonamide (467 mg) was then added as a suspension in DME (5 ml) and stirring was continued at 60° for 18 h. 2N Hydrochloric acid (2 ml) was then added and the mixture was heated under reflux for 5 h. The mixture was poured into 8% sodium bicarbonate solution (100 ml) and extracted with dichloromethane:ethanol (10:1; 4×50 ml). The combined, dried organic extracts were evaporated under reduced pressure to give a solid which was purified by FCC eluting with System A (100:10:1) to give the free base of the title compound (279 mg). The free base was dissolved in absolute ethanol (10 ml) and treated with a solution of maleic acid (100 mg) in absolute ethanol (2 ml). Ether (ca. 5 ml) was added to the solution, with cooling, to precipitate the title compound (265 mg), m.p. 145°–148°.

Analysis: Found: C,60.6; H,5.5; N,12.1;
$C_{19}H_{21}FN_4O.C_4H_4O_4$ requires C,60.5; H,5.5; N,12.3%.

EXAMPLE 16

6-Fluoro-2,3,4,5-tetrahydro-5-methyl-2-[(1,5-dimethyl-1H-imidazol-4-yl)methyl]-1H-pyrido[4,3-b]indol-1-one A stirred solution of 6-fluoro-2,3,4,5-tetrahydro-5-methyl-2-[(5-methyl-1H-imidazol -4-yl)methyl]-1H-pyrido[4,3-b]indol-1-one (347 mg) in dry DMF was treated with sodium hydride (73% dispersion in oil; 49 mg) and stirred under nitrogen for 30 min. The reaction mixture was then cooled to 0° and iodomethane (217 mg) was added dropwise. The reaction mixture was then allowed to warm to room temperature, with stirring being continued for 2 h. DMF was removed in vacuo and the residue was dissolved in dichloromethane (75 ml) and washed with water (3×75 ml) and brine (2×50 ml). The combined aqueous washings were extracted with dichloromethane (2×50 ml) and the combined organic extracts were dried and concentrated in vacuo to give an oil. This was dissolved in dichloromethane and adsorbed onto silica. Purification by FCC eluting with System A (200:10:1) gave a solid which was triturated with ether and then dried in vacuo to give the title compound (62 mg), m.p. 174°–175°.

$^1$H-N.m.r. δ 2.32 (3H,s), 3.08 (2H,t), 3.67 (2H,t), 3.69 (3H,s), 3.88 (3H,d), 4.63 (2H,s), 6.06 (2H,s), 7.02 (1H,dd), 7.12 (1H,dt), 7.78 (1H,d), 8.58 (1H,s).

EXAMPLE 17

6-Fluoro-2,3,4,5-tetrahydro-2-[(5-methyl-1H-imidazol-4-yl)methyl]-5-(2-propynyl)-1H-pyrido[4,3-b]indol-1-one maleate A stirred solution of 6-fluoro-2,3,4,5-tetrahydro-2-[[5-methyl-1-(triphenylmethyl) -1H-imidazol-4-yl]methyl]-1H-pyrido[4,3-b]indol-1-one (228 mg) in dry acetone (40 ml) and anhydrous potassium carbonate (116 mg) was treated with propargyl bromide (10% v/v solution in dry acetone; 1 ml) and heated at reflux overnight. After cooling, excess acetone was removed in vacuo, and the residue was partitioned between water (100 ml) and ethyl acetate (100 ml). The organic phase was washed with water (2×50 ml) and the combined aqueous extracts were washed with ethyl acetate (50 ml). The combined organic extracts were then concentrated in vacuo, and the residue was dissolved in a mixture of water (10 ml), glacial acetic acid (10 ml) and THF (15 ml) and heated to reflux for 2 h. The cooled solution was then basified with 2N sodium hydroxide (ca. 100 ml) and extracted with ethyl acetate (2×100 ml). The combined, dried organic extracts were adsorbed onto silica and purified by FCC eluting with System A (100:8:1) to give the free base of the title compound (95 mg). This was dissolved in the minimum hot dry methanol, and maleic acid (32 mg) was added. The solution was heated and then left to cool. Ether was added to precipitate the title compound (80 mg), m.p. 123°–124°.

Analysis: Found: C,60.9; H,4.7; N,12.0;
$C_{19}H_{17}FN_4O.C_4H_4O_4$ requires C,61.1; H,4.7; N,12.4%.

EXAMPLE 18

6-Fluoro-2,3,4,5-tetrahydro-2-[(5-methyl-1H-imidazol-4-yl)methyl]-5-(methylsulphonyl)-1H-pyrido[4,3-b]indol-1-one maleate A stirred solution of 6-fluoro-2,3,4,5-tetrahydro-2-[[5-methyl-1-(triphenylmethyl) -1H-imidazol-4-yl]methyl]-1H-pyrido[4,3-b]indol-1-one (64 mg) in dry DMF (10 ml) was treated with sodium hydride (73% dispersion in oil; 6 mg), and stirred under nitrogen for 30 min. Methanesulphonyl chloride (10% v/v solution in DMF; 1 ml) was added dropwise and the mixture was stirred for a further 45 min at room temperature. Additional sodium hydride (6 mg) and methanesulphonyl chloride solution (2 ml) were then added, and stirring was continued for 2 h. The mixture was then added to water (75 ml) and extracted with ethyl acetate (3×50 ml). The combined organic extracts were washed with water (2×50 ml) and brine (2×50 ml), dried and concentrated in vacuo to give a gum. This was dissolved in water (5 ml), glacial acetic acid (5 ml) and THF (5 ml), and heated to reflux for 2 h. The reaction mixture was then added to 2N sodium hydroxide (50 ml) and extracted with ethyl acetate (2×50 ml). The combined, dried organic extracts were adsorbed onto silica and purified by FCC eluting with System A (100:8:1) to give the free base of the title compound (24 mg). This was triturated with ether, and then dissolved in hot methanol (2 ml). Maleic acid (7.4 mg) was added, and the resulting solution was heated and then concentrated in vacuo to give an oil. This was triturated with ether to give the title compound (20 mg), m.p. 205°–208°.

$^1$H-N.m.r. δ 2.33 (3H,s), 3.37 (1H,t), 3.67 (2H,t), 3.82 (3H,s), 4.67 (2H,s), 6.07 (1H,s), 7.27 (1H,dd), 7.41 (1H,dt), 7.98 (1H,d), 8.7 (1H,s).

EXAMPLE 19

2,3,4,5-Tetrahydro-5-methyl-2-[(5-methyl-1H-imidazol-4-yl)methyl]-1-oxo-1H-pyrido[4,3-b]indole-6-carboxamide maleate A mixture of 6-cyano-2,3,4,5-tetrahydro-5-methyl-2-[(5-methyl-1H-imidazol-4-yl) methyl]-1H-pyrido[4,3-b]indol-1-one (100 mg), Amberlite resin IRA 400 OH) [made by stirring Amberlite resin IRA 400 (Cl) (0.88 g) in 2N sodium hydroxide (5 ml) at 21° for 2½ h, then filtering and washing with water (ca. 50 ml) until the water becomes neutral] and water (15 ml) was heated at reflux for 36 h. After this time, the water had evaporated and the resultant residue was stirred in hot ethanol (200 ml). The solid was then filtered off, placed in a Soxhlet and extracted with ethanol (250 ml) overnight. The combined ethanolic extracts were concentrated in vacuo and the residue was purified by FCC eluting with System A (100:8:1) to give the free base of the title compound (80 mg). A solution of the free base (80 mg) in methanol (50 ml) was treated with maleic acid (27 mg) and heated on a steam bath for 5 min. The solution was concentrated in vacuo, and a solution of the residue in methanol (10 ml) was treated with ether (ca. 80 ml) to precipitate the title compound (70 mg), m.p. 238°.

$^1$H-N.m.r. δ 2.37 (3H,s), 3.13 (2H,t), 3.67 (2H,t), 3.72 (3H,s), 4.67 (2H,s), 6.07 (2H,s), 7.1–7.3 (2H,m), 8.08 (1H,dd), 7.67 and 8.13 (2H, 2 x brs), 8.87 (1H,s).

EXAMPLE 20

Methyl 2,3,4,5-tetrahydro-5-methyl-2-[(5-methyl-1H-imidazol-4yl)methyl]-1-oxo-1H-pyrido[4,3-b]indole-5-propanoate maleate A solution of methyl 3-[2,3,4,5-tetrahydro-5-methyl-2-[(5-methyl-1H-imidazol -4-yl)methyl]-1-oxo-1H-pyrido[4,3-b]indol-1-yl]-2-propenoate 200 mg) in ethanol (50 ml) was hydrogenated at room temperature and atmospheric pressure over 10% palladium on carbon catalyst (50% aqueous paste; 20 mg) for 18 h. The mixture was then filtered, concentrated in vacuo, and the residue was purified by FCC eluting with System A (100:8:1) to give the free base of the title compound (70 mg). A portion of the free base (60 mg) in methanol (10 ml) was treated with maleic acid (18 mg), then heated on a steam bath for 10 min. The resultant solution was concentrated in vacuo and the residue was triturated with ether (10 ml) to give the title compound (70 mg), m.p. 205°.

T.l.c. (System A, 100:8:1) Rf 0.3.

EXAMPLE 21

2,3,4,5-Tetrahydro-6-hydroxy-5-methyl-2-[(5-methyl-1H-imidazol-4-yl)methyl]-1H-pyrido[4,3-b]indol-1-one maleate A solution of 2,3,4,5-tetrahydro-5-methyl-2-[(5-methyl-1H-imidazol-4-yl)methyl]-6-(phenylmethoxy)-1H-pyrido[4,3-b]indol-1-one (500 mg) in absolute ethanol (100 ml) was hydrogenated at room temperature and atmospheric pressure over 10% palladium on carbon catalyst (50% aqueous paste; 100 mg) for 6 h. The mixture was then filtered, concentrated in vacuo, and the resultant solid was recrystallised from ethanol (ca. 50 ml) to give the free base of the title compound (90 mg). Maleate formation using the method described in Example 20 gave the title compound (60 mg), m.p. 200°.

$^1$H-N.m.r. δ 2.37 (3H,s), 3.06 (2H,t), 3.65 (2H,t), 3.97 (3H,s), 4.65 (2H,s), 6.08 (2H,s), 6.58 (1H,d), 6.92 (1H,t), 7.45 (1H,d), 8.89 (1H,s).

EXAMPLE 22

6-Fluoro-2,3,4,5-tetrahydro-2-[(5-methyl-1H-imidazol-4-yl)methyl]-1H-pyrido [4,3-b]indol-1-one maleate A solution of 6-fluoro-2,3,4,5-tetrahydro-2-[(5-methyl-1H-imidazol-4-yl)-methyl]-5-(phenylmethoxymethyl)-1H-pyrido[4,3-b]indol-1-one (175 mg) in absolute ethanol (10 ml) and acetic acid (2.5 ml) was hydrogenated at room temperature and atmospheric pressure over 10% palladium on carbon catalyst (50% aqueous paste; 45 mg) in absolute ethanol (2 ml) for 20 h. More catalyst (45 mg) was added and stirring was continued for 20 h. The mixture was filtered and the filtrate was evaporated to dryness. The residue was treated with 8% sodium bicarbonate solution (50 ml) and extracted with dichloromethane (3×25 ml). the combined, dried organic extracts were evaporated to give an oil (ca. 130 mg) which was purified by FCC eluting with System A (150:10:1) to give the free base of the title compound (102 mg). This was dissolved in ethanol (ca. 2 ml) and treated with a solution of maleic acid (42 mg) in ethanol (0.5 ml). The solvent was removed in vacuo and the residue was triturated with dry ether (5×5 ml) to give the title compound (120 mg), m.p. 186°–188°.

Analysis: Found: C,57.8; H,4.7; N,13.2;
$C_{16}H_{15}FN_4O·C_4H_4O_4$ requires C,58.0; H,4.6; N,13.5%.

EXAMPLE 23

2,3,4,5-Tetrahydro-6-hydroxy-2[(5-methyl-1H-imidazol-4-yl)methyl]-1H-pyrido[4,3-b]indol-1-one maleate A solution of 2,3,4,5-tetrahydro-2-[(5-methyl-1H-imidazol-4-yl)methyl]-6-(phenylmethoxy)-5-[(phenylmethoxy)methyl]-1H-pyrido[4,3-b]indol-1-one (600 mg) in absolute ethanol (80 ml) and glacial acetic acid (4 ml) was hydrogenated at room temperature and atmospheric pressure over 10% palladium on carbon catalyst (50% aqueous paste; 100 mg) for 24 h. The mixture was then filtered and the filtrate was concentrated in vacuo. The residue was treated with 8% sodium bicarbonate solution (ca. 150 ml) and filtered. The filtered solid was then washed with water (ca. 100 ml), dissolved in ethanol (200 ml) and concentrated in vacuo to give a solid (320 mg) which was purified by FCC eluting with System A (100:8:1) to give the free base of the title compound (100 mg). A solution of the free base (100 mg) in methanol (20 ml) was treated with maleic acid (39 mg). The solution was heated on a steam bath for 10 min and concentrated in vacuo. A solution of the residue in methanol (2 ml) was treated with ether (ca. 80 ml) to give the title compound (100 mg), m.p. 130°.

T.l.c. (System A, 100:8:1) (2×elution) Rf 0.3.

EXAMPLE 24

6-Fluoro-2,3,4,5-tetrahydro-5-methyl-2-[(5-methyl-1H-imidazol-4-yl)methyl) -1H-pyrido[4,3-b]indol-1-one hydrochloride A solution of 6-fluoro-2,3,4,5-tetrahydro-5-methyl-2-[(5-methyl-1H-imidazol-4-yl) methyl]-1H-pyrido[4,3-b]indol-1-one (260 mg) in methanol (10 ml) was treated with ethereal hydrogen chloride and the mixture was then concentrated in vacuo. The residue was triturated with ether (15 ml) to give the title compound (230 mg) as a solid, m.p. 275°–278°.

Water Analysis Found 3.73% w/w≡0.75 mol H$_2$O.
Analysis: Found: C,55.8; H,5.3; N,15.2;
C$_{17}$H$_{17}$FN$_4$O.HCl.O.75H$_2$O requires C,56.3; H,5.4; N,15.4%.

EXAMPLE 25

6-Fluoro-2,3,4,5-tetrahydro-5-methyl-2-[(5-methyl-1H-imidazol-4-yl)methyl]-1H-pyrido[4,3-b]indol-1-one benzoate A solution of 6-fluoro-2,3,4,5-tetrahydro-5-methyl-2-[(5-methyl-1H-imidazol-4-yl) methyl]-1H-pyrido[4,3-b]indol-1-one (170 mg) in methanol (10 ml) was treated with benzoic acid (66 mg). Ether (ca. 20 ml) was added to precipitate a solid which was filtered off to give the title compound (220 mg), m.p. 169°–171°.

Analysis: Found: C,66.3; H,5.4; N,12.8;
C$_{17}$H$_{17}$FN$_4$O.C$_7$H$_6$O$_2$ requires C,66.3; H,5.3; N,12.9%.

EXAMPLE 26

6-Fluoro-2,3,4,5-tetrahydro-5-methyl-2-[(5-methyl-1H-imidazol-4-yl)methyl]-1H-pyrido[4,3-b]indol-1-one A solution of 6-fluoro-2,3,4,5-tetrahydro-5-methyl-1H-pyrido[4,3-b]indol-1-one (100 mg) in N-methylpyrrolidinone (10 ml) was treated with 4-toluenesulphonic acid monohydrate (17 mg) and 4-hydroxymethyl-5-methylimidazole hydrochloride (37 mg). The mixture was then heated to 125° for 18 h during which time three further portions of 4-hydroxymethyl-5-methylimidazole hydrochloride (37 mg) were added at 1,2 and 3 h respectively. The solution was then poured into 8% sodium bicarbonate solution (100 ml) and extracted with dichloromethane (3×100 ml). The combined extracts were concentrated in vacuo and the N-methylpyrrolidinone was distilled at 100°. The residue was purified by FCC eluting with System A (200:8:1) to give the title compound (100 mg), t.l.c. (System A, 100:8:1) Rf 0.3.

$^1$H-N.m.r. δ 2.36 (3H,s), 3.12 (2H,t), 3.67 (2H,t), 3.90 (3H,s), 4.66 (2H,s), 6.07 (2H,s), 6.95–7.2 (2H,m), 7.80 (1H,d), 8.80 (1H,s).

EXAMPLE 27

6-Fluoro-2,3,4,5-tetrahydro-5-methyl-2-[(5-methyl-1H-imidazol-4-yl)methyl]-1H-pyrido[4,3-b]indol-1-one A mixture of 6-fluoro-2,5-dihydro-5-methyl-2-[(5-methyl-1H-imidazol-4-yl)methyl]-1H-pyrido[4,3-b]indol-1-one (150 mg) and 10% palladium on carbon catalyst (50% aqueous paste; 75 mg) in absolute ethanol (30 ml) was hydrogenated at 80° and 80 p.s.i. for 24 h. The resulting suspension was filtered, and the filtrate evaporated to give a solid (190 mg) which was purified by HPLC (Spherisorb 55W, 25 cm×20 mm column eluting with hexane:ethanol: dichloromethane: 0.88 ammonia solution (65:25:10:1) to give the title compound (21 mg), m.p. 231°–233°.

The $^1$H-n.m.r. data obtained for this material were consistent with those obtained for the product of Example 26.

EXAMPLE 28

6-Fluoro-2,3,4,5-tetrahydro-5-methyl-2-[(5-methyl-1H-imidazol-4-yl)methyl -1H-pyrido[4,3-b]indol-1-one 4-[2-(2-Fluorophenyl)-2-methylhydrazino]-5,6-dihydro-1-](5-methyl-1H-imidazol -4-yl)methyl]-2(1H)-pyridinone (65 mg) was treated with concentrated sulphuric acid (0.5 ml) and left standing for 5 min. The solution was then neutralised with 8% sodium bicarbonate solution (30 ml) and extracted with dichloromethane:ethanol (5:1) (3×15 ml). The combined, dried organic extracts were evaporated to give an oil (52 mg) which was purified by FCC eluting with System A (200:10:1) to give the title compound (3 mg), t.l.c. (System A, 200:10:1) Rf 0.28.

The $^1$H-n.m.r. data obtained for this material were consistent with those obtained for the product of Example 26.

EXAMPLE 26

6-Fluoro-2,3,4,5-tetrahydro-5-methyl-2-[(5-methyl-1H-imidazol-4-yl)methyl]-1H-pyrido[4,3-b]indol-1-one A mixture of 6-fluoro-2,3,4,5-tetrahydro-5-methyl-2-[(4-methyloxazol-5-yl) methyl]-1H-pyrido[4,3-b]indol-1-one (180 mg) and formamide (20 ml) was heated at 180° for 18 h. The solution was then cooled (0°), diluted with water (100 ml) and extracted with dichloromethane (3×100 ml). The combined extracts were concentrated in vacuo and purified by FCC eluting with System A (100:8:1) to give the title compound (110 mg), m.p. 230°–233°.

The $^1$H-n.m.r. data obtained for this material were consistent with those obtained for the product of Example 26.

EXAMPLE 30

6-Fluoro-2,3,4,5-tetrahydro-5-methyl-2-[(5-methyl-1H-imidazol-4-yl)methyl]-1H-pyrido[4,3-b]indol-1-one A stirred solution of 4-[(6-fluoro-2,3,4,5-tetrahydro-5-methyl-1-oxo-1H-pyrido [4,3-b]indol-2-yl)methyl]-N,N,5-trimethyl-1H-imidazole-1-sulphonamide (92 mg) in absolute ethanol (5 ml) was treated with 2N hydrochloric acid (20 ml) and stirred under nitrogen at 100°–110° for 6 h, and then cooled. 2N Sodium hydroxide (60 ml) was added, and the mixture was extracted with ethyl acetate (2×75 ml). The combined, dried organic extracts were concentrated in vacuo to give a solid (71 mg) which was purified by FCC eluting with System A (100:8:1) to give the title compound (57 mg), m.p. 233°-234°.

The $^1$H-n.m.r. data obtained for this material were consistent with those obtained for the product of Example 26.

EXAMPLE 31

6-Fluoro-2,3,4,5-tetrahydro-5-methyl-2-[(5-methyl-1H-imidazol-4-yl)methyl]-1H-pyrido[4,3-b]indol-1-one A solution of 2,3-dichloro-5,6-dicyano-1,4-benzoquinone (133 mg) in THF (4 ml) was added dropwise to a stirred solution of 6-fluoro-2,3,4,5-tetrahydro-5-methyl-2-[(5-methyl-1H-imidazol-4-yl)methyl]-1Hpyrido[4,3-b]indole (70 mg) in THF (12 ml) at −10° under nitrogen, and stirring was continued for 4 h. Water (20 ml) was then added, and the resulting solution was left to stand overnight. Excess THF was removed in vacuo, and the resultant aqueous solution was extracted with ethyl acetate (3×50 ml). The combined, dried organic extracts were adsorbed onto silica and purified by FCC eluting with System A (100:10:1) to give the title compound (15 mg), m.p. 231.5°-233°.

The $^1$H-n.m.r. data obtained for this material were consistent with those obtained for the product of Example 26.

EXAMPLE 32

6-Fluoro-2,3,4,5-tetrahydro-5-methyl-2-[(5-methyl-1H-imidazol-4-yl)methyl]-1H-pyrido[4,3-b]indol-1-one A stirred solution of 6-fluoro-2,3,4,5-tetrahydro-2-[[5-methyl-1-(triphenylmethyl) -1H-imidazol-4-yl]methyl]-1H-pyrido[4,3-b]indol-1-one (100 mg) in dry DMF (15 ml) was treated with sodium hydride (73.2% dispersion in oil; 10.5 mg) and stirred under nitrogen at room temperature for 20 min. Methyl iodide (2.3% v/v solution in dry DMF; 1 ml) was added and the solution was stirred for a further 20 min. The reaction mixture was then added to water (100 ml) and extracted with ethyl acetate (2×50 ml). The combined organic extracts were washed with water (2×100 ml), dried and concentrated in vacuo to give a solid. This solid was dissolved in THF (10 ml), water (10 ml) and glacial acetic acid (10 ml) an heated at reflux for 3 h. THF was removed in vacuo, and the remaining solution was added to 2N sodium hydroxide (pH+14) and extracted with ethyl acetate (3×50 ml). The combined, dried organic extracts were adsorbed onto silica and purified by FCC eluting with System A (100:8:1) to give the title compound (45 mg), m.p. 234°-235°.

The $^1$H-n.m.r. data obtained for this material were consistent with those obtained for the product of Example 26.

EXAMPLE 33

6-Fluoro2,3,4,5-tetrahydro-5-methyl-2-[(5-methyl-1H-imidazol-4-yl)methyl]-1H-pyrido[4,3-b]indol-1-one A solution of 6-fluoro-2,3,4,5-tetrahydro-2-[[1-(methoxyethyl)-5-methyl -1H-imidazol-4-yl]methyl]-5-methyl-1H-pyrido[4,3-b]indol-1-one and 6-fluoro-2,3,4,5-tetrahydro-2-[[1-(methoxymethyl)-4-methyl-1H-imidazol-5-yl]methyl]-5-methyl-1H-pyrido[4,3-b]indol-1-one (32 mg) in 47% aqueous hydrobromic acid (4 ml) was heated on a steam bath for ca. 2 h. After cooling, the reaction mixture was added to 2N sodium hydroxide (50 ml) and extracted with ethyl acetate (2×50 ml). The combined, dried organic extracts were adsorbed onto silica and purified by FCC eluting with System A (100:8:1) to give the title compound (6.5 mg), m.p. 229°-232°.

The $^1$H-n.m.r. data obtained for this material were consistent with those obtained for the product of Example 26.

EXAMPLE 34

6-Fluoro-2,3,4,5-tetrahydro-5-methyl-2-[(5-methyl-1H-imidazol-4-yl)methyl]-1H-pyrido[4,3-b]indol-1-one A solution of phenylmethyl 4-[(6-fluoro-2,3,4,5-tetrahydro-5-methyl-1-oxo-1H-pyrido [4,3-b]indol-2-yl)methyl]-5-methyl-1H-imidazole-1-carboxylate (100 mg) in ethanol (20 ml) and 2N hydrochloric acid (10 ml) was heated on a steam bath for 10 min. The cooled reaction mixture was then added to water (5 ml) and 2N sodium hydroxide (20 ml), and extracted with ethyl acetate (2×75 ml). The combined, dried organic extracts were adsorbed onto silica and purified by FCC eluting with System A (100:8:1) to give a solid which was triturated with ether to give the title compound (50 mg), m.p. 232°-233°.

The $^1$H-n.m.r. data obtained for this material were consistent with those obtained for the product of Example 26.

The following examples illustrate pharmaceutical formulations according to the invention, containing 6-fluoro-2,3,4,5-tetrahydro-5-methyl-2-[(5-methyl-1H-imidazol-1-yl)methyl]-1H-pyrido[4,3−b]-indol-1-one as the active ingredient. Physiologically acceptable salts and/or solvates of this compound, and other compounds of formula (I) and their physiologically acceptable salts and/or solvates may be formulated in a similar manner.

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

Direct Compression

| Tablet | mg/tablet |
|---|---|
| Active Ingredient | 1.00 |
| Anhydrous Lactose USNF* | 79.00 |
| Microcrystalline Cellulose USNF* | 19.55 |
| Magnesium Stearate BP | 0.45 |
| Compression weight | 90.00 |

*of a grade suitable for direct compression.

The active ingredient is passed through a 60 mesh sieve, blended with the anhydrous lactose, microcrystalline cellulose and magnesium stearate. The resultant mix is compressed into tablets using a suitable tablet machine fitted with 5.5 mm diameter punches.

Tablets of other strengths may be prepared by altering the ratio of active ingredient to lactose or the compression weight and using punches to suit.

| Sub-Lingual Tablet | mg/tablet |
|---|---|
| Active Ingredient | 1.0 |
| Compressible Sugar NF | 64.0 |
| Magnesium Stearate BP | 0.5 |

| Sub-Lingual Tablet | mg/tablet |
|---|---|
| Compression Weight | 65.0 |

The active ingredient is sieved through a suitable sieve, blended with the excipients and compressed using suitable punches.

Tablets of other strengths may be prepared by altering either the ratio of active ingredient to excipients or the compression weight and using punches to suit.

Wet Granulation

| Conventional Tablet | mg/tablet |
|---|---|
| Active Ingredient | 1.0 |
| Lactose BP | 153.0 |
| Starch BP | 30.0 |
| Pregelatinised Maize Starch BP | 15.0 |
| Magnesium Stearate BP | 1.5 |
| Compression Weight | 200.0 |

The active ingredient is sieved through a suitable sieve and blended with lactose, starch and pregelatinised maize starch. Suitable volumes of purified water are added and the powders are granulated. After drying, the granules are screened and blended with the magnesium stearate. The granules are then compressed into tablets using 7 mm diameter punches.

Tables of other strengths may be prepared by altering the ratio of active ingredient to lactose or the compression weight and using punches to suit.

| Sub-Lingual Tablet | mg/tablet |
|---|---|
| Active Ingredient | 1.0 |
| Mannitol BP | 58.0 |
| Hydroxypropylmethylcellulose | 5.0 |
| Magnesium Stearate BP | 1.0 |
| Compression Weight | 65.0 |

The active ingredient is sieved through a suitable sieve and blended with the mannitol and hydroxypropylmethylcellulose. Suitable volumes of purified water are added and the powders re granulated. After drying, the granules are screened and blended with the magnesium stearate. The granules are compressed into tablets using suitable punches.

Tablets of other strengths may be prepared by altering the ratio of active ingredient to mannitol or the compression weight and punches to suit.

| CAPSULES | mg/capsule |
|---|---|
| Active Ingredient | 1.0 |
| *Starch 1500 | 98.0 |
| Magnesium Stearate BP | 1.0 |
| Fill Weight | 100.0 |

*a form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

In the above examples of tablets and capsules, when the active ingredient is included as a suitable salt, the quantity of the major excipient used is adjusted accordingly.

SYRUP

This may be either a sucrose or sucrose free presentation.

| A. Sucrose Syrup | mg/5 ml dose |
|---|---|
| Active Ingredient | 1.0 |
| Sucrose BP | 2750.0 |
| Glycerine BP | 500.0 |
| Buffer | |
| Flavour | |
| Colour | as required |
| Preservative | |
| Purified Water BP to | 5.0 ml |

The active ingredient, buffer, flavour, colour and preservative are dissolved in some of the water and the glycerine is added. The remainder of the water is heated to dissolve the sucrose and is then cooled. The two solutions are combined, adjusted to volume and mixed. The syrup is clarified by filtration.

| B. Sucrose-Free | mg/5 ml dose |
|---|---|
| Active Ingredient | 1.0 |
| Hydroxypropylmethylcellulose USP (viscosity type 4000) | 22.5 |
| Buffer | |
| Flavour | |
| Colour | as required |
| Preservative | |
| Sweetener | |
| Purified Water BP to | 5.0 ml |

The hydroxypropylmethylcellulose is dispersed in hot water, cooled and then mixed with an aqueous solution containing the active ingredient and the other components of the formulation. The resultant solution is adjusted to volume and mixed. The syrup is clarified by filtration.

INJECTION FOR INTRAVENOUS ADMINISTRATION

| | mg/ml | |
|---|---|---|
| Active Ingredient | 0.05 | 0.5 |
| Sodium Chloride BP | as required | as required |
| Water for Injection BP to | 1.0 ml | 1.0 ml |

Sodium chloride may be added to adjust the tonicity of the solution and the pH may be adjusted, using acid or alkali, to that of optimum stability and/or facilitate solution of the active ingredient. Alternatively, suitable buffer salts may be used.

The solution is prepared, clarified and filled into appropriate size ampoules sealed by fusion of the glass. The injection is sterilised by heating in an autoclave using one of the acceptable cycles. Alternatively, the solution may be sterilised by filtration and filled into sterile ampoules under aseptic conditions. The solution may be packed under an inert atmosphere of nitrogen or other suitable gas.

METERED DOSE PRESSURISED AEROSOL

| Suspension Aerosol | mg/metered dose | Per can |
|---|---|---|
| Active Ingredient micronised | 0.050 | 12.0 mg |
| Lecithin USNF | 0.020 | 4.80 mg |
| Trichlorofluoromethane BP | 23.64 | 5.67 g |
| Dichlorodifluoromethane BP | 61.25 | 14.70 g |

The active ingredient is micronised in a fluid energy mill to a fine particle size range. The lecithin is mixed with the trichlorofluoromethane at a temperature of 10°–15° C. and the micronised drug is mixed into the solution with a high shear mixer. The suspension is metered into aluminium aerosol cans and suitable metering valves, delivering 85 mg of suspension are crimped onto the cans and the dichlorodifluoromethane is pressure filled into the cans through the valves.

Solution Aerosol

| | mg/metered dose | Per can |
|---|---|---|
| Active Ingredient | 0.05 | 12.0 mg |
| Ethanol BP | 7.500 | 1.80 g |
| Trichlorofluoromethane BP | 18.875 | 4.53 g |
| Dichlorodifluoromethane BP | 48.525 | 11.65 g |

Oleic acid BP, or a suitable surfactant e.g. Span 85 (sorbitan trioleate) may also be included).

The active ingredient is dissolved in the ethanol together with the oleic acid or surfactant if used. The alcoholic solution is metered into suitable aerosol containers followed by the trichlorofluoromethane. Suitable metering valves are crimped onto the containers and dichlorodifluoromethane is pressure filled into them through the valves.

Inhalation Cartridges

| | mg/cartridge |
|---|---|
| Active Ingredient (micronised) | 0.05 |
| Lactose BP to | 25.00 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler.

| SUPPOSITORY | |
|---|---|
| Active Ingredient | 1.0 mg |
| *Witepsol H15 to | 1.0 g |

*Witepsol H15 is a proprietary grade of Adeps Solidus Ph. Eur.

A suspension of the active ingredient is prepared in the molten Witepsol and filled, using suitable machinery, into 1 g size suppository moulds.

We claim:

1. A compound of formula (I)

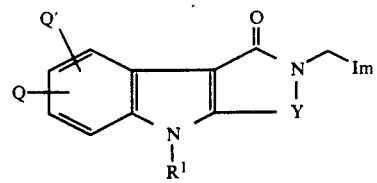

wherein Im represents an imidazolyl group of the formula:

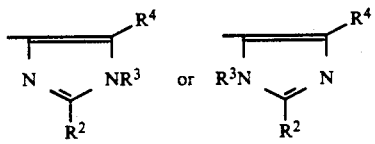

and $R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkylC$_{1-4}$alkyl-, phenyl, phenylC$_{1-3}$alkyl-, $-CO_2R^5$, $-COR^5$, $-CONR^5R^6$ or $-SO_2R^5$ (wherein $R^5$ and $R^6$, which may be the same or different, each represents a hydrogen atom, a $C_{1-6}$alkyl or $C_{3-7}$cycloalkyl group, or a phenyl or phenylC$_{1-4}$alkyl- group, in which the phenyl group is optionally substituted by one or more $C_{1-4}$alkyl, $C_{1-4}$alkoxy or hydroxy groups or halogen atoms, with the proviso that $R^5$ does not represent a hydrogen atom when $R^1$ represents a group $-CO_2R^5$ or $-SO_2R^5$);

one of the groups represented by $R^2$, $R^3$ and $R^4$ is a hydrogen atom or a $C_{1-6}$alkyl, $C_{3-7}$cycloalkyl, $C_{3-6}$alkenyl, phenyl or phenylC$_{1-3}$alkyl- group, and each of the other two groups, which may be the same or different, represents a hydrogen atom or a $C_{1-6}$alkyl group;

Y represents the group CH=CH or $(CH_2)_n$, wherein n represents 2 or 3;

Q represents a halogen atom, or a group selected from hydroxy, $C_{1-4}$alkoxy, phenylC$_{1-3}$alkoxy-, $C_{1-6}$alkyl, cyano, phenyl which may be unsubstituted or substituted by one or more $C_{1-4}$alkyl, $C_{1-4}$alkoxy or hydroxy groups or halogen atoms, $-NR^7R^8$, $-CONR^7R^8$ or $-(CH_2)_pCONR^7R^8$ (wherein $R^7$ and $R^8$, which may be the same or different, each represents a hydrogen atom or a $C_{1-4}$alkyl or $C_{3-4}$alkenyl group; and p represents 1, 2 or 3), $-(CH_2)_qNR^9R^{10}$ (wherein $R^9$ represents a hydrogen atom or a $C_{1-4}$alkyl group, and $R^{10}$ represents a group $-COR^{11}$ or $-SO_2R^{11}$ wherein $R^{11}$ represents a $C_{1-4}$alkyl group; and q represents 0, 1, 2 or 3), or $-(CH_2)_2CO_2R^{11}$($R^{11}$ being as defined previously);

Q' represents a hydrogen or a fluorine atom;

or a physiologically acceptable salt or solvate thereof.

2. A compound according to claim 1 in which $R^1$ represents a hydrogen atom or a $C_{1-6}$alkyl, $C_{3-4}$alkynyl, $C_{4-6}$cycloalkylmethyl, or $C_{1-3}$alkylsulphonyl group.

3. A compound according to claim 1 in which $R^2$, $R^3$ and $R^4$ each independently represent a hydrogen atom or a $C_{1-4}$alkyl group.

4. A compound according to claim 1 in which Q represents a halogen atom or a hydroxy, $C_{1-4}$alkoxy, phenylC$_{1-3}$alkoxy-, $C_{1-6}$alkyl, cyano, phenyl, $-CONH_2$, or $-(CH_2)_2CO_2CH_3$ group.

5. A compound according to claim 1 in which Q represents a halogen atom, or a hydroxy, phenylC$_{1-3}$alkoxy-, C$_{1-3}$alkyl or cyano group.

6. A compound according to claim 1 in which Q represents a fluorine atom.

7. A compound according to claim 1 in which R$^1$ represents a hydrogen atom or a C$_{1-4}$alkyl, C$_{3-4}$alkynyl or C$_{4-6}$cycloalkylmethyl group; R$^2$ and R$^3$ each represent a hydrogen atom; R$^4$ represents a C$_{1-4}$alkyl group; and Q represents a halogen atom or a hydroxy, phenylC$_{1-3}$alkoxy-, C$_{1-3}$alkyl or cyano group.

8. A compound according to claim 1 in which Y represents the group (CH$_2$)$_2$ and Q' is a hydrogen atom.

9. The compound according to claim 1 which is: 6-fluoro-2,3,4,5-tetrahydro-5-methyl-2-[(5-methyl-1H-imidazol-4-yl) methyl]-1H-pyrido[4,3-b]indol-1-one or a physiologically acceptable salt and solvate thereof.

10. A compound according to claim 1 selected from the group consisting of:
2,3,4,5-tetrahydro-5,6-dimethyl-2-[(5-methyl-1H-imidazol-4-yl) -methyl]-1H-pyrido[4,3—b]indol-1-one;
6,9-difluoro-2,3,4,5-tetrahydro-5-methyl-2-[(5-methyl-1H-imidazol-4-yl) methyl]-1H-pyrido[4,3—b]indol-1-one;
6-fluoro-2,3,4,5-tetrahydro-2-[(5-methyl-1H-imidazol-4-yl) methyl]-5-(2-propynyl)-1H-pyrido[4,3—b]indol-1-one;
2,3,4,5-tetrahydro-5-methyl-2-[(5-methyl-1H-imidazol-4-yl) methyl]-1-oxo-1H-pyrido[4,3—b]indole-6-carbonitrile;
or a physiologically acceptable salt or solvate thereof.

11. A pharmaceutical composition which comprises an effective amount of a compound of formula (I) as defined in claim 1 or a physiologically acceptable salt or solvate thereof together with at least one physiologically acceptable carrier or excipient.

12. A pharmaceutical composition according to claim 11 in a form adapted for oral or parenteral administration.

13. A pharmaceutical composition according to claim 11 in which the active ingredient is 6-fluoro-2,3,4,5-tetrahydro-5-methyl-2[(5-methyl -1H-imidazol-4-yl)methyl]-1H-pyrido[4,3-b]indol-1-one or a physiologically acceptable salt or solvate thereof.

14. A pharmaceutical composition according to claim 13 in a form adapted for oral or parenteral administration.

15. A method of treating a condition which may be ameliorated by the antagonism of 5HT$_3$ receptors which comprises administering to a patient an effective amount to relieve said condition of a compound of formula (I) as defined in claim 1 or a physiologically acceptable salt or solvate thereof.

16. A method according to claim 15 in which said compound is 6-fluoro-2,3,4,5-tetrahydro-5-methyl-2[(5-methyl-1H-imidazol -4-yl)methyl]-1H-pyrido[4,3-b]indol-1-one or a physiologically acceptable salt or solvate thereof.

17. A method according to claim 16 for the treatment of nausea and vomiting.

18. A method according to claim 16 for the treatment of nausea and vomiting.

19. A method according to claim 16 for the treatment of irritable bowel syndrome.

20. A method according to claim 16 for the treatment of dyspepsia.

* * * * *

UNITED STATES PATENT AND TRADEMARK OFFICE
CERTIFICATE OF CORRECTION

PATENT NO. : 5,183,820

DATED : February 2, 1993

INVENTOR(S) : Ian H. COATES et al.

It is certified that error appears in the above-identified patent and that said Letters Patent is hereby corrected as shown below:

Column 42, claim 17, line 1, delete "16" and insert —15—.

Signed and Sealed this

Fourteenth Day of December, 1993

Attest:

BRUCE LEHMAN

Attesting Officer  Commissioner of Patents and Trademarks